US006326466B1

(12) United States Patent
Bottaro et al.

(10) Patent No.: US 6,326,466 B1
(45) Date of Patent: Dec. 4, 2001

(54) DOUBLE-STRANDED RNA DEPENDENT PROTEIN KINASE DERIVED PEPTIDES TO PROMOTE PROLIFERATION OF CELLS AND TISSUES IN A CONTROLLED MANNER

(75) Inventors: Donald P. Bottaro, Kensington, MD (US); Raymond Petryshyn, Hume, VA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/230,548

(22) PCT Filed: Jul. 29, 1997

(86) PCT No.: PCT/US97/14350

§ 371 Date: Jul. 23, 1999

§ 102(e) Date: Jul. 23, 1999

(87) PCT Pub. No.: WO98/04717

PCT Pub. Date: Feb. 5, 1998

Related U.S. Application Data

(60) Provisional application No. 60/023,307, filed on Jul. 30, 1996.

(51) Int. Cl.[7] .................... A61K 38/00; C07K 16/00; C07K 17/00; C07K 5/00; C07K 7/00

(52) U.S. Cl. .................... 530/324; 530/300; 530/328; 530/329; 530/330; 530/333; 514/2

(58) Field of Search .................... 536/23.1, 24.3, 536/24.5; 530/300, 324, 328, 329, 330, 333; 514/2

(56) References Cited

U.S. PATENT DOCUMENTS 5,670,330 * 9/1997 Sonenberg et al. .................... 435/15

FOREIGN PATENT DOCUMENTS

WO 96/39806 * 12/1994 (WO) .
WO 95/22245 * 8/1995 (WO) .

OTHER PUBLICATIONS

Feng et al., Identification of double stranded RNA binding domains in the in the interferon–induced double stranded RNA–activated p68 kinase, PNAS (89), pp. 5447–5451, Jun. 1992.*
Icely et al., TIK, a novel serine/threonine kinase is recognized by antibodies directed against phosphotyrosine, The Journal of Biological Chemistry, vol. 266 (24), pp. 16073–16077, 1991.*
Tanaka et al., Mechanism of interferon action: Structure of the mouse PKR encoding the interferon inducible RNA–dependent protein kinase, PNAS, vol. 91, pp. 7995–7999, Aug. 1994.*
Tanaka et al., Sequence of the murine interferon inducible RNA dependent protein kinase (PKR) deduced from genomic clones, Gene, 153, pp. 283–4, 1995.*
Kuhen et al., Mechanism of interferon action: Sequence of the human interferon–inducible RNA–dependent protein kinase (PKR) deduced from genomic clones, Gene 178, pp. 191–193, 1996.*
Meurs et al., Molecular cloning and characterization of the human double stranded RNA activated protein kinase induced by interferon, Cell, v9olume 62, pp. 379–390, Jul. 1997.*
Thomis et al., Mechanism of Interferon Action: cDNA Structure, Expression, and Regukation of teh Interferon Induced, RNA Dependent P1/elf–2alpha, Protein Kinase from Human Cells, Virology 188, pp. 33–46, 1992.*
Gatignol et al., Characterization of Human TAR RNA–Binding Protein that Activated the HIV–1 LTR, Science 251, pp. 1597–1599, Mar. 1991.*
Lee et al., A Testis Cytoplasmic RNA Binding Protein that has the properties of a translation repressor, Molecular and Cellular Biology, vol. 16(6), pp. 3023–3034, 1996.*
Rice et al., Discovery and in Vitro Development of AIDS Antiviral Biopharmaceuticals, Advances in Pharmacology, vol. 33, pp. 389–438, 1995.*
Bowie et al., Deciphering teh Message in Protein sequences: Tolerance to Amino Acid Substitutions, Science vol. 247, pp. 1306–1310, 1990.*
Burgess et al., Possible Dissociation of teh Heparin Binding and Mitgenic Activities of Heparin Binding (Acidic Fibroblast) Growth Factor–1 from it's Receptor–binding Activities by Site Directed Mutagenesis of a Single Lysine Residue., The Journal of Cell, 1990.*
Bork, Powers and Pitfalls in Sequence Analysis: The 70% Hurdle, Genome Research, 10: pp. 398–400, 2000.*
Lazar et al., Transforming Growth Factor Alpha: Mutation of aspartic Acid 47 and Leucine 48 Results in Different Biological Activities, Molecular and Cellular Biology, vol. 8, No. 3, pp. 1247–1252, 1988.*
Dermer, Biotechnology, vol. 12, p. 320, Mar. 1994.*

(List continued on next page.)

Primary Examiner—Anita G.
Assistant Examiner—Jennifer Hunt
(74) Attorney, Agent, or Firm—Townsend and Townsend and Crew LLP

(57) ABSTRACT

This invention relates to double-stranded RNA dependent protein kinase (PKR) peptide antagonists. More specifically, the invention relates to compositions and methods for antagonizing activation of double-stranded RNA dependent protein kinase (PKR) to stimulate eukaryotic cell proliferation. The invention relates to compositions and methods to inhibit activation of double-stranded RNA dependent protein kinase (PKR) to stimulate cell proliferation under conditions of cell cycle arrest, quiescence, reduced growth or cell death. The invention also relates to methods of protecting cells from HIV-1 pathogenesis using inhibitors of PKR.

47 Claims, No Drawings

OTHER PUBLICATIONS

Judware R. et al., Inhibition of the dsRNA–Dependent Protein Kinase By A Peptide Derived From the Human Immunodeficiency Virus Type 1 Tat Protein, Journal of Interferon Research, vol. 13, No. 2, Apr. 1993, pp. 153–160.

Patel R. and Sen G., Characterization of the Interactions Between Double–Stranded RNA and the Double–Stranded RNA Binding Domain of the Interferon Induced Protein Kinase, Cellular and Molecular Biology Research, vol. 40, No. 7/8, 1994.

Patel R. et al., Role of the Amino–Terminal Residues fo the Interferon–Induced Protein Kinase in its Activation by Double–Stranded RNA and Heparin, The Journal of Biological Chemistry, vol. 269, No. 28, Jul. 15, 1994, pp. 18593–98.

Feng G. et al., Indentification of Double–Stranded RNA–Binding Domains in the Interferon–Induced Double–Standed RNA–Activated p68 Kinase, PNAS USA, vol. 89, No. 12, Jun. 15, 1992, pp 5447–5451.

Patel R. and Sen G., Indentification of the Double–Stranded RNA–Binding Domain of the Human Interferon–Inducible Protein Kinase, The Journal of Biological Chemistry, vol. 267, No. 11, Apr. 15, 1992, pp 7671–76.

Lin Y. et al., Inhibition of Nuclear Translocation of Transcription Factor NF–kB By A Synthetic Peptide Containing A Cell Membrane–Permeable Motif and Nuclear Localization Sequence, The Journal of Biological Chemistry, vol. 270, No. 24, Jun. 16, 1995, pp. 14255–58.

Maitra R. et al., HIV–1 TAR RNA Has An Intrinsic Ability to Activate Interferon–Inducible Enzymes, Virology, vol. 204, No. 21 Nov. 1994, pp 823–827.

Nekhai S. et al., Peptides Derived From the Interferon–Induced PKR Prevent Activation by HIV–1 TAR RNA, Virology, vol. 222, No. 1, Aug. 1, 1996, pp. 193–200.

Judware R. et al., Inhibition of the dsRNA–Dependent Protein Kinase By A Peptide Derived From the Human Immunodeficiency Virus Type 1 Tat Protein, Journal of Interferon Research, vol. 13, No. 2, Apr. 1993, pp 153–160.

Patel R. and Sen G., Characterization of the Interactions Between Double–Stranded RNA and the Double–Stranded RNA Binding Domain of the Interferon Induced Protein Kinase, Cellular and Molecular Biology Research, vol. 40, No. 7/8, 1994.

Patel R. et al., Role of the Amino–Terminal Residues of the Interferon–Induced Protein Kinase in its Activation by Double–Stranded RNA and Heparin, The Journal of Biological Chemistry, vol. 269, No. 28, Jul. 15, 1994, pp 18593–98.

Feng G. et al., Identification of Double–Stranded RNA–Binding Domains in the Interferon–Induced Double–Stranded RNA–Activated p68 Kinase, PNAS USA, vol. 89, No. 12, Jun. 15, 1992, pp 5447–5451.

Patel R. and Sen G., Identification of the Double–Stranded RNA–Binding Domain of the Human Interferon–Inducible Protein Kinase, The Journal of Biological Chemistry, vol. 267, No. 11, Apr. 15, 1992, pp 7671–76.

Lin Y. et al., Inhibition of Nuclear Translocation of Transcription Factor NF–kB By A Synthetic Peptide Containing A Cell Membrane–Permeable Motif and Nuclear Localization Sequence, The Journal of Biological Chemistry, vol. 270, No. 24, Jun. 16, 1995, pp 14255–58.

Maitra R. et al., HIV–1 TAR RNA Has An Intrinsic Ability to Activate Interferon–Inducible Enzymes, Virology, vol. 204, No. 21 Nov. 1994, pp 823–827.

Nekhai S. et al., Peptides Derived From the Interferon–Induced PKR Prevent Activation by HIV–1 TAR RNA, Virology, vol. 222, No. 1, Aug. 1, 1996, pp 193–200.

* cited by examiner

SEQUENCE LISTING

<160> NUMBER OF SEQ ID NOS: 31

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist, murine PKR site 1

<400> SEQUENCE: 1

Ala Lys Gly Arg Ser Lys Gln Glu Ala Arg
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist

<400> SEQUENCE: 2

Gly Glu Gly Arg Ser Lys Lys Glu Ala Lys
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist

<400> SEQUENCE: 3

Gly Ser Gly Ser Thr Lys Gln Glu Ala Lys
 1               5                  10

-continued

```
<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist

<400> SEQUENCE: 4

Gly Ser Gly Val Thr Lys Gln Glu Ala Lys
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist

<400> SEQUENCE: 5

Gly Ser Gly Thr Ser Lys Lys Leu Ala Lys
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist

<400> SEQUENCE: 6

Gly Thr Gly Ser Thr Lys Gln Glu Ala Lys
 1               5                  10

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist

<400> SEQUENCE: 7

Lys Gly Arg Ser Lys Gln Glu Ala Arg
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist, consensus PKR sequence

<400> SEQUENCE: 8

Gly Arg Ser Lys Gln Glu Ala Arg
 1               5

<210> SEQ ID NO 9
<211> LENGTH: 8
<212> TYPE: PRT
<213> ORGANISM: Artificial Sequence
```

```
<220> FEATURE:
<223> OTHER INFORMATION: Description of Artificial Sequence:
      double-stranded RNA dependent protein kinase (PKR) peptide
      antagonist

<400> SEQUENCE: 9

Gly Arg Ser Lys Lys Glu Ala Lys
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist

<400> SEQUENCE: 10

Gly Ser Thr Lys Gln Glu Ala Lys
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist

<400> SEQUENCE: 11

Gly Val Thr Lys Gln Glu Ala Lys
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist

<400> SEQUENCE: 12

Gly Thr Ser Lys Lys Leu Ala Lys
 1               5

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist, murine PKR site 1 (R1-peptide)

<400> SEQUENCE: 13

Ala Lys Gly Arg Ser Lys Gln Glu Ala Arg Asn Ala Ala Ala Lys Leu
 1               5                  10                  15

Ala Val Asp Ile Leu
            20

<210> SEQ ID NO 14
<211> LENGTH: 23
<212> TYPE: PRT
<213> ORGANISM: Artificial Sequence
<220> FEATURE:
```

```
<223> OTHER INFORMATION: Description of Artificial Sequence:
      double-stranded RNA dependent protein kinase (PKR) peptide
      antagonist, murine/human PKR site 2

<400> SEQUENCE: 14

Tyr Gly Thr Gly Ser Gly Ser Thr Lys Gln Glu Ala Lys Gln Leu Ala
 1               5                  10                  15

Ala Lys Glu Ala Tyr Gln Lys
            20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist, human PKR site 1 (hR1 peptide)

<400> SEQUENCE: 15

Lys Lys Glu Ala Lys Asn Ala Ala Ala Lys Leu Ala Val Glu Ile Leu
 1               5                  10                  15

Asn Lys Glu Lys Lys
            20

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist, murine PKR site 2

<400> SEQUENCE: 16

Lys Gln Glu Ala Lys Gln Leu Ala Ala Lys Glu Ala Tyr Gln Lys Leu
 1               5                  10                  15

Leu Lys

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist, human TAR RNA binding protein region

<400> SEQUENCE: 17

Gly Ser Gly Thr Ser Lys Lys Leu Ala Lys Arg Asn Ala Ala Ala Lys
 1               5                  10                  15

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist

<400> SEQUENCE: 18

Tyr Ser Ile Gly Thr Gly Ser Thr Lys Gln Glu Ala Lys Gln Leu Ala
 1               5                  10                  15

Ala Lys Leu Ala Tyr Leu Gln Ile
            20
```

```
<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence:exemplary
      cell-membrane permeable peptide

<400> SEQUENCE: 19

Ala Ala Val Ala Leu Leu Pro Ala Val Leu Leu Ala Leu Leu Ala Pro
 1               5                  10                  15

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist, cell-membrane permeable peptide

<400> SEQUENCE: 20

Ala Ala Val Ala Leu Leu Pro Ala Val Leu Leu Ala Leu Leu Ala Pro
 1               5                  10                  15

Lys Gly Arg Ser Lys Gln Glu Ala Arg
            20                  25

<210> SEQ ID NO 21
<211> LENGTH: 24
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist, cell-membrane permeable peptide

<400> SEQUENCE: 21

Ala Ala Val Ala Leu Leu Pro Ala Val Leu Leu Ala Leu Leu Ala Pro
 1               5                  10                  15

Gly Arg Ser Lys Gln Glu Ala Arg
            20

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence:peptide 271

<400> SEQUENCE: 22

Asp Met Leu Pro Lys Lys Ser Glu Glu Ser Ala Ala Pro Ser Arg
 1               5                  10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence:peptide 273

<400> SEQUENCE: 23

Ser Ser Ala Ala Arg Pro Ser Gly Arg Arg Asp Pro Ala Gly
 1               5                  10                  15

<210> SEQ ID NO 24
```

```
<211> LENGTH: 21
<212> TYPE: PRT
<213> ORGANISM: Artificial Sequence
<220> FEATURE:
<223> OTHER INFORMATION: Description of Artificial Sequence:peptide 274,
      random R1 peptide

<400> SEQUENCE: 24

Lys Gly Ser Lys Asn Ala Leu Ala Ala Arg Val Ile Ala Ala Ala Gln
 1               5                  10                  15

Arg Glu Leu Lys Asp
            20

<210> SEQ ID NO 25
<211> LENGTH: 46
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist with cell permeability, heme agglutinin-epitope tag and
      PKR peptide antagonist subsequences

<400> SEQUENCE: 25

Ala Ala Val Ala Leu Leu Pro Ala Val Leu Leu Ala Leu Leu Ala Pro
 1               5                  10                  15

Tyr Pro Tyr Asp Val Pro Asp Tyr Ala Lys Lys Glu Ala Lys Asn Ala
            20                  25                  30

Ala Ala Lys Leu Ala Val Glu Ile Leu Asn Lys Glu Lys Lys
        35                  40                  45

<210> SEQ ID NO 26
<211> LENGTH: 26
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist, human PKR site 1

<400> SEQUENCE: 26

Gly Glu Gly Arg Ser Lys Lys Glu Ala Lys Asn Ala Ala Ala Lys Leu
 1               5                  10                  15

Ala Val Glu Ile Leu Asn Lys Glu Lys Lys
            20                  25

<210> SEQ ID NO 27
<211> LENGTH: 24
<212> TYPE: PRT
<213> ORGANISM: Artificial Sequence
<220> FEATURE:
<223> OTHER INFORMATION: Description of Artificial Sequence:human PKR
      52-75

<400> SEQUENCE: 27

Glu Pro Glu Gly Glu Gly Arg Ser Lys Lys Glu Ala Lys Asn Ala Ala
 1               5                  10                  15

Ala Lys Leu Ala Val Glu Ile Leu
            20

<210> SEQ ID NO 28
<211> LENGTH: 24
<212> TYPE: PRT
<213> ORGANISM: Artificial Sequence
<220> FEATURE:
<223> OTHER INFORMATION: Description of Artificial Sequence:human PKR
```

-continued

```
       137-160

<400> SEQUENCE: 28

Tyr Gly Thr Gly Ser Gly Val Thr Lys Gln Glu Ala Lys Gln Leu Ala
  1               5                  10                  15

Ala Lys Glu Ala Tyr Gln Lys Leu
             20

<210> SEQ ID NO 29
<211> LENGTH: 24
<212> TYPE: PRT
<213> ORGANISM: Artificial Sequence
<220> FEATURE:
<223> OTHER INFORMATION: Description of Artificial Sequence:human PKR
      142-165

<400> SEQUENCE: 29

Tyr Ser Ile Gly Thr Gly Ser Thr Lys Gln Glu Ala Lys Gln Leu Ala
  1               5                  10                  15

Ala Lys Leu Ala Tyr Leu Gln Ile
             20

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence:murine PKR
      51-74

<400> SEQUENCE: 30

Glu Pro Glu Ala Lys Gly Arg Ser Lys Gln Glu Ala Arg Asn Ala Ala
  1               5                  10                  15

Ala Lys Leu Ala Val Asp Ile Leu
             20

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence:
      double-stranded RNA dependent protein kinase (PKR) peptide
      antagonist, cell-permeable PKR peptide antagonist

<400> SEQUENCE: 31

Ala Ala Val Ala Leu Leu Pro Ala Val Leu Leu Ala Leu Leu Ala Pro
  1               5                  10                  15

Lys Lys Glu Ala Lys Asn Ala Ala Ala Lys Leu Ala Val Glu Ile Leu
             20                  25                  30

Asn Lys Glu Lys Lys
         35
```

DOUBLE-STRANDED RNA DEPENDENT PROTEIN KINASE DERIVED PEPTIDES TO PROMOTE PROLIFERATION OF CELLS AND TISSUES IN A CONTROLLED MANNER

This application is a continuation-in-part of U.S. Provisional Application No. 60/023,307, filed on Jul. 30, 1996, the text of which is incorporated by reference herein in its entirety.

This invention was made with U.S. Government support pursuant to Contract No. CA42717-07 awarded by the National Cancer Institute, National Institutes of Health. The U.S. Government has certain rights in this invention.

FIELD OF THE INVENTION

The invention relates to compositions and methods to inhibit activation of double-stranded RNA dependent protein kinase (PKR) to stimulate cell proliferation under conditions of cell cycle arrest, quiescence, reduced growth or cell death. The invention also relates to methods of protecting cells from HIV-1 pathogenesis using inhibitors of PKR.

BACKGROUND OF THE INVENTION

Double-stranded RNA dependent protein kinase (alternatively, "PKR") is a serine/threonine protein kinase which exerts antiviral and anticellular functions. It can be induced by interferon (Meurs, et al., Cell 62:379–390 (1990); Sen, et al. J. Biol. Chem. 267:5017–5020 (1992); Hovanessian, A. G., J. Interferon Res. 9:641–647 (1989)). PKR is involved in regulating a number of physiologic processes. These include cell growth and differentiation (Petryshyn, et al., Proc. Natl. Acad. Sci. USA 85:1427–1431 (1988); Petryshyn, et al., J. Biol. Chem. 259:14736–14742 (1984); Judware, et al., Mol. Cell. Biol. 11:3259–3267 (1991), tumor suppression (Koromilas, et al., Science 257:1685–1689 (1992); Meurs, et al., Proc. Natl. Acad. Sci. USA 90:232–236 (1993)), and modulation of signal transduction pathways (Leonardo, et al., Cell 57:287–294 (1989); Kumar, et al., Proc. Natl. Acad. Sci. U.S.A. 91:6288–6292 (1994); Maran, et al., Science 265:789–792 (1994)).

These cellular effects of PKR have generally been attributed to translational regulation (Farrell, et al., Cell 11:187–200 (1977); Petryshyn, et al., Methods Enzymol. 99:346–362 (1983); Samuel, C. E., Proc. Natl. Acad. Sci. U.S.A. 76:600–604 (1979)). In the presence of low concentrations of double-stranded RNA (dsRNA), divalent cations and ATP, PKR undergoes a phosphorylation which is required to convert the enzyme from a latent to an active protein kinase (Edery, et al., Cell 56:303–312 (1989); Lebleu, et al., Proc. Natl. Acad. Sci. USA 73:3107–3111 (1976); Petryshyn, et al., Methods Enzymol. 99:346–362 (1983)). Paradoxically, the phosphorylation and activation is prevented by high concentrations of dsRNA (Farrell, et al., Cell 11:187–200 (1977); Hunter, et al., J. Biol. Chem. 250:7887–7891 (1975)). Once activated, PKR phosphorylates the alpha subunit of the eukaryotic initiation factor 2 (eIF-2 alpha) (Farrell, et al., Cell 11:187–200 (1977); Lebleu, et al., Proc. Nat. Acad. Sci. USA 73:3107–3111 (1976); Petryshyn, et al., Methods Enzymol. 99:346–362 (1983)), which in turn, results in inhibition of protein synthesis (London, et al. (Boyer, et al. (eds)), The Enzymes, vol. 18. Academic Press, New York (1987); Hershey, J. W., J. Biol. Chem. 264:20823–20826 (1989)). The antiviral effect of PKR is believed to be mediated the phosphorylation of eIF-2 alpha. However, it is not known whether PKR's anticellular effect is due to phosphorylation of eIF-2 alpha, 1 kappa B or another unknown substrate (Lee, et al. Virology 231:81–88 (1997)).

The mechanism by which PKR interacts with dsRNA is unclear. Neither the spatial, structural or sequence requirements within the RNA or the protein itself are sufficiently resolved to fully understand the dynamics of this interaction. Since a diverse group of viral RNAs interact and modulate the activity of PKR (Clarke, et al., Nucleic Acids Res. 19:243–248 (1991); Kitajewski, et al., Cell 45:195–200 (1986); Hovanessian, A. G., J. Interferon Res. 9:641–647 (1989); Hunter, et al., J. Biol. Chem. 250:7887–7891 (1975); SenGupta, et al. Nucleic Acids Res. 17:969–978 (1989); Roy, et al., J. Virol 65:632–640 (1991); Edery, et al., Cell 56:303–312 (1989); Judware, et al., J. Interferon Res. 13:153–160 (1993); Biscboff, et al., Virology 172:106–115 (1989)), there does not appear to be sequence specificity. However, there is a dependency on both the length of the double-strandedness and its secondary structure (Manche, et al., Mol. Cell. Biol. 12:5238–5248 (1992); Ghadge, et al., J. Virol. 68:4137–4151 (1994); Hunter, et al., J. Biol. Chem. 250:7887–7891 (1975); Edery, et al., Cell 56:303–312 (1989)). Tertiary structure is also likely to be important. Several viral RNAs inhibit the activation of PKR (Kitajewski, et al., Cell 45:195–200 (1986); Clarke, et al., Nucleic Acids Res. 19:243–248 (1991); Ghadge, et al., J. Virol. 68:4137–4151 (1994)), while others are efficient activators (Hovanessian, A. G., J. Interferon Res. 9:641–647 (1989)). The TAR sequence of HIV-1 mRNA transcript has been shown to both activate (Edery, et al., Cell 56:303–312 (1989); SenGupta, et al. Nucleic Acids Res. 17:969–978 (1989); Judware, et al., J. Interferon Res. 13:153–160 (1993)) and prevent activation (Gunnery, et al., Proc. Natl. Acad. Sci. USA 87:8687–8691 (1990)) of PKR at low concentrations.

Both human (Meurs, et al., Cell 62:379–390 (1990)) and murine PKR (Feng, et al., Proc. Natl. Acad. Sci. USA 89: 5447–5451 (1992); Baier, et al., Nucleic Acids Res. 21:4830–4835 (1993)) have been cloned and sequenced and these two cDNAs share extensive nucleotide sequence identity (Feng, et al., Proc. Natl. Acad. Sci. USA 89: 5447–5451 (1992)). Results from several studies have reported that the RNA-binding domain of PKR is localized to the N-terminal portion of the kinase. Feng, et al., Proc. Natl. Acad. Sci. USA 89: 5447–5451 (1992); McCormack, et al., Virology 188:47–56 (1992); Patel, et al., J. Biol. Chem. 269:18593–18598 (1994); Green, et al., Genes Dev. 6:2478–2490 (1992); Patel, et al., J. Biol. Chem. 267:7671–7676 (1992). Although deletions of several short portions of PKR sequence rich in positively charged residues have been shown to diminish dsRNA-induced PRK activation, no discrete PKR region or amino acid sequence motif which is both necessary and sufficient to bind to regulatory dsRNA was known prior to this invention (Feng, et al., Proc. Natl. Acad. Sci. USA 89: 5447–5451 (1992)).

Thus, prior to this invention, the existence of a defined linear, non-conformationally dependent dsRNA-binding region of PKR, which is both necessary and sufficient to bind to dsRNA, was unknown.

Furthermore, PKR antagonists were unknown. As PKR is a regulator of cell quiescence and cell death, such antagonists would be valuable for treating diseases or conditions associated with premature or induced cell death, such as the T cell depletion due to HIV-1 infection.

Thus, there exists a great need for inhibitors of PKR. The present invention fulfills these and other needs.

SUMMARY OF THE INVENTION

The invention relates to compositions and methods to inhibit activation of double-stranded RNA dependent protein kinase (PKR) to stimulate cell proliferation under conditions of cell cycle arrest, quiescence, reduced growth or cell death. The invention also relates to methods of protecting cells from HIV-1 pathogenesis using inhibitors of PKR. The invention further relates to methods for inhibiting apoptosis mediated by PKR.

In one aspect, the present invention is directed to an isolated protein kinase double-stranded RNA dependent protein kinase (PKR) peptide antagonist of less than about 50 amino acid residues in length and comprising at least about 8 contiguous amino acid residues from a sequence selected from the group consisting of: SEQ ID NO:1, SEQ ID NO:2, SEQ ID NO:3, SEQ ID NO:4, SEQ ID NO:5, and SEQ ID NO:6, or a conservatively modified variant thereof, wherein said variant forms a complex with regulatory RNA. In another embodiment of the invention, the peptide of claim 1 includes at least about 9 contiguous residues from the sequence or a conservatively modified variant thereof. In alternative embodiments, the invention includes: the peptide of claim 1, wherein said peptide comprises the sequences of claim 1 or a conservatively modified variant thereof; and, the peptide of claim 1, wherein said peptide is the sequence shown in SEQ ID NO:1, SEQ ID NO:2, SEQ ID NO:3, SEQ ID NO:4, SEQ ID NO:5, or SEQ ID NO:6.

In an additional embodiment, the invention includes the peptide of claim 1 comprising no more than about 25 amino acids. In another embodiment, the invention includes the peptide of claim 3, wherein said peptide comprises the cell-permeable peptide shown in SEQ ID NO:19.

Another embodiment of the invention includes an isolated nucleic acid encoding a double-stranded RNA dependent protein kinase (PKR) peptide antagonist of less than about 50 amino acid residues in length comprising at least about 8 contiguous amino acid residues from a sequence selected from the group consisting of: SEQ ID NO:1, SEQ ID NO:2, SEQ ID NO:3, SEQ ID NO:4, SEQ ID NO:5, and SEQ ID NO:6, or a conservatively modified variant thereof, wherein said conservatively modified variant forms a complex with regulatory RNA.

In an additional embodiment, the invention includes an expression vector comprising a nucleic acid encoding a double-stranded RNA dependent protein kinase (PKR) peptide antagonist peptide of less than about 50 amino acid residues in length comprising at least about 8 contiguous amino acid residues from a sequence selected from the group consisting of: SEQ ID NO:1, SEQ ID NO:2, SEQ ID NO:3, SEQ ID NO:4, SEQ ID NO:5, and SEQ ID NO:6, or a conservatively modified variant thereof, wherein said variant forms a complex with regulatory RNA. The invention also includes a host cell comprising the expression vector of claim 8.

Another embodiment of the invention includes a method of antagonizing regulatory RNA binding to double-stranded RNA dependent protein kinase (PKR), said method comprising contacting a PKR peptide antagonist of less than about 50 amino acids in length with a regulatory RNA to form a regulatory RNA-antagonist complex, wherein said peptide is inclusive of at least 8 contiguous amino acid residues from a sequence selected from the group consisting of: SEQ ID NO:1, SEQ ID NO:2, SEQ ID NO:3, SEQ ID NO:4, SEQ ID NO:5, and SEQ ID NO:6, or a conservatively modified variant thereof.

In an additional embodiment, the invention includes the method of claim 9, wherein the peptide includes at least 9 contiguous residues from the sequence or a conservatively modified variant thereof. In a further embodiments, the invention includes: the method of claim 9, wherein said peptide includes the sequence of SEQ ID NO:1, SEQ ID NO:2, SEQ ID NO:3, SEQ ID NO:4, SEQ ID NO:5, and SEQ ID NO:6, or a conservatively modified variant thereof; and, the method of claim 9, wherein said peptide is the sequence of SEQ ID NO:1, SEQ ID NO:2, SEQ ID NO:3, SEQ ID NO:4, SEQ ID NO:5, and SEQ ID NO:6.

In a further embodiment, the invention includes the method of claim 9, wherein said peptide comprises the cell-permeable peptide shown in SEQ ID NO:19; and, the method of claim 9, wherein said method comprises contacting said antagonist with a regulatory RNA within a eukaryotic cell.

In an additional embodiment, the invention includes the method of claim 14, wherein said antagonist is expressed by an expression vector encoding said antagonist; and, the method of claim 14, wherein said method stimulates cell proliferation under conditions of cell cycle arrest, quiescence, reduced growth or cell death. In further embodiments, the invention includes the method of claim 14, wherein said method is ex vivo, and the method of claim 14, wherein said method is in vivo.

In a further embodiment, the invention includes the method of claim 9, wherein said peptide antagonist comprises no more than about 25 amino acids.

Another embodiment of the invention includes the method of claim 14, wherein the cell is a human cell; and, the method of claim 14, wherein the method reduces cell death. The invention also includes the method of claim 21, wherein the method reduces cell death by reducing cell lysis caused by a viral infection; and, the method of claim 22, wherein said viral infection is an HIV-1 infection. The invention further includes the method of claim 21, wherein cell death is reduced by inhibiting apoptosis.

In an additional embodiment, the invention includes a method of inhibiting apoptosis by antagonizing regulatory RNA binding to double-stranded RNA dependent protein kinase (PKR), said method comprising contacting a PKR peptide antagonist of less than about 50 amino acids in length with a regulatory RNA to form a regulatory RNA-antagonist complex, wherein said peptide is inclusive of at least 8 contiguous amino acid residues from a sequence selected from the group consisting of: SEQ ID NO:1, SEQ ID NO:2, SEQ ID NO:3, SEQ ID NO:4, SEQ ID NO:5, and SEQ ID NO:6, or a conservatively modified variant thereof.

In one embodiment, the invention includes a method of increasing expression of CD4 or maintaining the expression of CD4 on the cell surface of CD4$^+$-expressing cells, said method comprising contacting a PKR peptide antagonist of less than about 50 amino acids in length with a regulatory RNA to form a regulatory RNA-antagonist complex, wherein said peptide is inclusive of at least 8 contiguous amino acid residues from a sequence selected from the group consisting of: SEQ ID NO:1, SEQ ID NO:2, SEQ ID NO:3, SEQ ID NO:4, SEQ ID NO:5, and SEQ ID NO:6, or a conservatively modified variant thereof.

In a further embodiment, the invention includes a method to detect the presence or absence of a mutant PKR in a cell comprising contacting a biological sample, under stringent hybridization conditions, with a nucleic acid probe capable of selectively hybridizing to a PKR nucleic acid sequence to form a hybridization complex; and detecting the formation of the hybridization complex as an indication of the presence or absence of a mutant PKR polynucleotide sequence in the sample. The invention further includes the method of claim 30, wherein the presence or absence of a mutation in a PKR determines a predisposition to a malignancy due to expression of a mutant PKR.

Another embodiment of the invention includes a kit for to rapidly determine the presence in a biological sample of PKR which is unable to form a complex with regulatory RNA, comprising a stable preparation of a nucleic acids of claim 7; a hybridization solution in either dry or liquid form for the hybridization of probes to target PKR nucleic acids; a solution for washing and removing undesirable and non-hybridized nucleic acids; a substrate for detecting the hybridization complex; and, instructions for performing and interpreting the assay.

A further embodiment of the invention includes an antibody which is specifically reactive with a PKR peptide antagonist, where the peptide antagonist comprises a recombinant or synthetic peptide of at least seven amino acids in length selected from amino acid subsequences of each of the sequences selected from the group consisting of SEQ ID NOS: 1 through 6. The invention also includes a method of antagonizing regulatory RNA binding to double-stranded RNA dependent protein kinase (PKR), said method comprising contacting the antibody of claim 33 to a PKR. In another embodiment, the invention includes the method of claim 34, where the method comprises contacting the antibody with a PKR within a eukaryotic cell.

A further understanding of the nature and advantages of the present invention may be realized by reference to the remaining portions of the specification, the figures and claims.

DETAILED DESCRIPTION

The present invention provides peptide antagonists of double-stranded RNA dependent protein kinase (PKR) which inhibit the activation of PKR by regulatory RNA and, consequently, are permissive of the proliferation of cells under conditions which would otherwise induce quiescence, reduced growth or cell death. Thus, in a preferred embodiment, the PKR antagonists of the invention are administered to provide protection of cells from death. In additional embodiments, the PCR antagonists are administered to provide protection from the excessive cell death caused by human immunodeficiency virus type 1 (HIV-1).

In one embodiment of the invention, the peptide antagonists can be used as cell culture reagents to stimulate expression of recombinant proteins. The peptide antagonists can be used to stimulate proliferation of eukaryotic cells, particularly mammalian cells such as mice, rats, rabbits, sheep, goats, pigs, and more preferably, of primate cells, including human cells.

In various embodiments, the peptide antagonists of the invention can be administered in vivo or ex vivo. The PKR peptide antagonists of the invention also have therapeutic utility in, for example, stimulating wound healing or for ex vivo proliferation of dermal fibroblasts and/or immature keratinocytes for use in skin grafts.

All publications, patents and patent applications cited herein are hereby expressly incorporated by reference for all purposes.

I. DEFINITIONS

Units, prefixes, and symbols as used herein may be denoted in their SI designated form. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Amino acid sequences are written left to right in the direction of amino to carboxy terminus, respectively. Nucleic acid sequences are written left to right in the direction of 5' to 3', respectively. All numerical ranges indicated herein are inclusive of the starting and ending number. Although any methods and materials similar or equivalent to those described herein can be used in the practice or testing of the present invention, the preferred methods and materials are described. For purposes of the present invention, the following terms are defined below.

By "PKR" is meant the protein having the function of, and alternatively referred to as, the proteins: "double-stranded RNA dependent protein kinase", "double-stranded RNA dependent eIF-2 alpha kinase", "DAI" (Jimenez-Garcia, et al., *J. Cell Sci.* 106:11–12 (1993)), "dSI", "p68 kinase" (Lee, et al., *J. Interferon Cytokine Res.* 16:1073–1078 (1996)), or dsRNA-PK. See also, Clemens, et al., *J. Interferon Res.* 13:241 (1993).

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

As used herein, "contact" or "contacting" means to place in direct physical association under physiological conditions. Physiological conditions are those which support cell viability and biosynthesis. Typically, physiological conditions also support the proliferation of cells. Contacting a regulatory RNA with a PKR antagonist permits formation of a regulatory RNA-peptide antagonist complex. Typically, contacting takes place within a eukaryotic cell either in vivo or ex vivo.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a finctionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See Creighton (1984) *Proteins* W.H. Freeman and Company.

The invention also provides the means for one of skill to identify additional PKR antagonists that include "conservatively modified variants" of exemplified antagonists of the invention by routine finctional assays, including: an eIF-2 alpha-specific protein kinase assay as described by Katze et al., *Mol. Cell. Biol.* 11:5497–5505 (1991); and, a PKR phosphorylation assay, where PKR phosphorylation is reduced relative to a control assay lacking a PKR peptide antagonist, as described by Judware and Petryshyn, *Mol. Cell. Biol.* 11:3259–3267 (1991).

Thus, the PKR peptide antagonists of the invention are members of a family (genus) of double-stranded RNA (dsRNA) ("regulatory RNA") PKR-derived binding domains, or motifs, which are homologous, which share substantial sequence similarity, ie., structural features which are common to all members of this PKR-derived peptide genus, and which have common functional properties, i.e., possessing the ability to bind to dsRNA and to function as a PKR antagonist, as described below. The terms "sequence identity," "sequence similarity" and "homology" in the context of this invention mean that two peptide sequences, when optimally aligned, such as by the programs BLAST, GAP or BESTFIT using default gap weights, share at least 40 percent sequence identity, preferably at least 50 percent sequence identity, and most preferably at least 60 percent sequence identity. "Percentage amino acid sequence identity" refers to a comparison of the amino acid sequences of two polypeptides which, when optimally aligned, have approximately the designated percentage of the same amino acids. For example, "60% sequence identity" and "60% homology" refer to a comparison of the amino acid sequences of two polypeptides which when optimally aligned have 60% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The terms "isolated" or "biologically pure" refer to material which is substantially or essentially free from components which normally accompany it as found in its naturally occurring environment. The isolated material optionally comprises material not found with the material in its natural environment.

An "expression vector" includes a recombinant expression cassette which includes a nucleic acid which can be transcribed and translated by a cell. A recombinant expression cassette is a nucleic acid construct, generated recombinantly or synthetically, with a series of specified nucleic acid elements which permit transcription of a particular nucleic acid in a target cell. The expression vector can be part of a plasmid, virus, or nucleic acid fragment. Typically, the recombinant expression cassette portion of the expression vector includes a nucleic acid to be transcribed, and a promoter.

By "host cell" is meant a cell which contains an expression vector and supports the replication or expression of the expression vector. A host cell can be prokaryotic cells such as *E. coli*, or eukaryotic cells such as yeast, insect, or mammalian cells.

The term "peptide" is meant to include not only polypeptides comprising amino acids linked together by peptide bonds but any form of peptidomimetic and any form of chemical linkage to form the polypeptide/peptidomimetic structure (such as peptidosulfonamides), as described, for example, in Chorev, et al., *TibTech* 13:438 (1995); de Bont, et al., *Bioorganic & Medicinal Chemistry* 4:667–672 (1996); Bohm, H., *J. of Computer-Aided Molec. Design* 10:265–272 (1996).

By "peptide antagonist" or "PKR peptide antagonist" is meant a polymeric molecule built up from at least seven amino acid, or amino-acid-like residues (as, for example, peptidomimetics) linked to each other by, for example, peptide bonds. The peptide antagonists of the invention compete with PKR for binding to regulatory RNA. The peptide antagonists are unable to activate PKR. The peptide antagonists function to "antagonize regulatory RNA binding" to PKR by forming a "regulatory RNA-peptide antagonist complex".

By "cell-permeable peptide" is meant a peptide which when conjugated to a peptide antagonist and placed externally and in contact with a cell, enables the peptide antagonist to be transported into the cell at a higher rate than a peptide antagonist not conjugated to a cell-permeable peptide.

By "complex" or "regulatory RNA-antagonist complex" or "regulatory RNA-peptide antagonist complex" is meant a physical association between regulatory RNA and a peptide antagonist such that the kinase activity of PKR is diminished, as compared to the activity of a PKR without the presence of PKR antagonist. The regulatory RNA-antagonist complex formation can be measured directly, as by RNA mobility shift assays, as described below. Alternatively, the formation and antagonistic activity of the complex can be measured using any variety of protein kinase assays, including PKR autophosphorylation or PKR substrate phosphorylation assays. If determining the complex formation by its ability to inhibit PKR phosphorylation of a substrate, an eIF-1 alpha phosphorylation assay can be used. If complex forms for a sufficient length of time such that eIF-2 alpha phosphorylation is reduced by at least 5%, preferably at least 10%, more preferably at least 15%, relative to a control assay lacking a peptide antagonist as determined by an eIF-2 alpha-specific protein kinase assay, see, e.g., Katze et al., *Mol. Cell. Biol.* 11:5497–5505 (1991), then a PKR-inhibitory regulatory RNA-antagonist complex has formed. Alternatively, complex formation can be assessed if PKR phosphorylation is reduced by at least 5%, preferably at least 10%, more preferably at least 15%, relative to a control assay lacking a peptide antagonist as determined by an PKR phosphorylation, see, e.g., Judware and Petryshyn, *Mol. Cell. Biol.* 11:3259–3267 (1991).

By "regulatory RNA" is meant an RNA comprising any form of double-stranded RNA structure, whether formed by intrastrand or interstrand annealing, which activates PKR. This activation can be caused by the binding of the regulatory RNA directly to a region of the PKR. Activated PKR functions has a variety of functions, including causing increase levels of phosphorylated eIF-2 alpha, 1 kappa B, or PKR auto-phosphorylation in eukaryotic cells by at least 5%, more preferably at least 10%, and preferably at least 15% as determined in an eIF-2 alpha-specific protein kinase assay or a PKR phosphorylation assay, respectively. See, e.g., Katze et al., and Judware and Petryshyn, supra. Exemplary regulatory RNA includes poly-riboinosine (50 bases long): poly-ribocytosine (50 bases long), reovirus dsRNA, and HIV-1 TAR RNA. See, e.g., Hovanassian, *J. Interferon. Res.*, 9:641–647 (1989). Regulatory RNA may be non-xenogenic (i.e., non-viral) and endogenous to a cell, or, of xenogenic origin.

By "contiguous amino acid residues from the sequence" in the context of a specified number of amino acid residues, is meant a sequence of amino acids of the specified number from within the specified reference sequence which has the identical order of amino acids and the same adjacent peptides as in the reference sequence.

By "stimulates cell proliferation" is meant decreasing the cell doubling time by at least 10%, preferably at least 15%, and more preferably at least 20%, and/or increasing cell density by at least 10%, preferably by at least 15%, and more preferably by at least 20% relative to controls lacking the peptide antagonist as determined by cell proliferation and DNA synthesis assays (See, e.g., Zwijsen et al., *Mol. Cell. Biol.* 16:2554–2560 (1996)).

By "under conditions of cell cycle arrest" is meant conditions that, in the absence of a peptide antagonist, induce cell quiescence. A quiescent cell is one that is not passing through the cell cycle. Cells under cell cycle arrest are sometimes said to be in $G_0$ phase.

By "ex vivo" is meant outside the body of the organism from which a cell or cells is obtained or from which a cell lineage is isolated. Ex vivo applications may comprise use of intact cells, or employ a cell-free system (i.e., in vitro) such as a lysate.

By "in vivo" is meant within the body of the organism from which the cell was obtained or from which a cell lineage is isolated.

By "human cell" is meant a cell isolated from humans at any stage of development.

By "regulatory RNA binding to PKR" is meant the association and resultant activation of PKR by regulatory RNA.

The term "residue" or "amino acid residue" or "amino acid" as used herein refers to an amino acid that is incorporated into a protein, polypeptide, or peptide (collectively "peptide"). The amino acid may be a naturally occurring amino acid and, unless otherwise limited, may encompass known analogs of natural amino acids that can finction in a similar manner as naturally occurring amino acids.

The term "apoptosis" or "programed cell death" is meant to refer toa self-destruct process most metazoan animals can activate. Once the process is triggered, or the cells are committed to undergoing apoptosis, the cells undergo various defined morphological and physiological changes including cell shrinkage, chromatin condensation, membrane blebbing, and DNA degradation into a characteristic oligonucleosomal ladder composed of multiples of 200 base pairs, leading eventually to cell death. In apoptosis, or "programmed cell death" a series of lethal events for the cell appear to be generated directly as a result of transcription of cellular DNA. Thus, apoptosis is a physiologic means for cell death. For example, lymphocytes exposed to glucocorticoids die by apoptosis. Involution of hormone sensitive tissue such as breast and prostate that occurs when the trophic hormone is removed occurs via apoptosis.

The term "CD4$^+$-expressing cell" means any cell which expresses on its cell surface the polypeptide known in the art as CD4, including but not limited to lymphoctes such as T cells, macrophages, dendritic cells, cancer cells, and the like.

PKR Peptide Antagonists

The isolated PKR peptide antagonists of the present invention comprise at least about 5, 6, 7, or 8, and typically at least 9 or 10 contiguous amino acid residues from within the sequence represented by single letter amino acid code: AKGRSKQEAR (SEQ ID NO:1), GEGRSKKEAK (SEQ ID NO:2), GSGSTKQEAK (SEQ ID NO:3), GSGVTKQEAK (SEQ ID NO:4), GSGTSKKLAK (SEQ ID NO:5), GTGSTKQEAK (SEQ ID NO:6), or conservatively modified variants thereof. In preferred embodiments, the peptide antagonists of the invention comprise one or more of the sequences: KGRSKQEAR (SEQ ID NO:7); GRSKQEAR (SEQ ID NO:8); GRSKKEAK (SEQ ID NO:9), GSTKQEAK (SEQ ID NO:10), GVTKQEAK (SEQ ID NO:11), GTSKKLAK (SEQ ID NO:12).

The conservatively modified variants of PKR peptide antagonists of SEQ ID NOS:1 through 12, are preferably inclusive of the glutamine (E), lysine (K) and/or arginine (R) residues present in the position indicated in the unmodified sequences of SEQ ID NOS:1 through 12 (i.e., from the sequence that the conservatively modified variant is a variant of) and more preferably further inclusive of the alanine (A) residues present in the position indicated in the unmodified sequence.

In some embodiments, the PKR peptide antagonists comprise at least N contiguous amino acid residues from the sequence: AKGRSKQEARNAAAKLAVDIL (SEQ ID NO:13) where at least 5 of the N contiguous amino acids residues are of SEQ ID NO:1. "N" as used herein represents any one of the integers selected from the group consisting of from 5 to the number of amino acid residues in the referenced sequence, inclusive. In other embodiments, the PKR peptide antagonists comprise at least N contiguous amino acid residues from the sequence: YGTGSGSTKQEAKQ-LAAKEAYQK (SEQ ID NO:14) where at least 5 of the N contiguous amino acids residues are of SEQ ID NO:3.

In further ernbodiments, the PKR peptide antagonists comprise at least N contiguous amino acid residues from the sequence: KKEAKNAAAKLAVEILNKEKK (SEQ ID NO:15) where at least 5 of the N contiguous amino acids residues are of SEQ ID NO:2. In additional embodiments, the PKR peptide antagonists comprise at least N contiguous amino acid residues from the sequence: KQEAKQ-LAAKEAYQKLLK (SEQ ID NO:16) where at least 5 of the N contiguous amino acids residues are of SEQ ID NO:3. In further embodiments, the PKR peptide antagonists comprise at least N contiguous amino acid residues from the sequence: GSGTSKKLAKRNAAAK (SEQ ID NO:17) where at least 5 of the N contiguous amino acid residues are of SEQ ID NO:5. In still further embodiments, the PKR peptide antagonists comprise at least N contiguous amino acid residues from the sequence: YSIGTGSTKQEAKQ-LAAKLAYLQI (SEQ ID NO:18) where at least 5 of the N contiguous amino acids residues are of SEQ ID NO:6. In yet another embodiment, the PKR peptide antagonists comprise at least N contiguous amino acid residues from the sequence: GEGRSKKEAKNAAAKLAVEILNKEKK (SEQ ID NO:26) where at least 5 of the N contiguous amino acids residues are of SEQ IDNO:2.

The nucleic acid and amino acid sequences of murine and human PKR are known in the art; numbering of amino acid residues is according to Feng et al., *Proc. Natl. Acad. Sci. USA*, 89:5447–5451 (1992). See also, Meurs et al., *Cell*, 62:378–380 (1990); Baier et al., *Nucl. Acids. Res.*, 21:4830–4835 (1993).

PKR peptide antagonists also include peptides of at least 7, preferably 8, and more preferably 9 or 10 amino acid residues in length which are substantially identical to a PKR peptide antagonist of one of the sequences of SEQ ID NOS: 1 through 6. The term "substantial identity" or "substantially identical" in the context of a peptide indicates that a peptide comprises a sequence with at least 80% sequence identity to a reference sequence, or preferably 85%, or more preferably 95% sequence identity to the reference sequence over a comparison window of about 7–10 amino acid residues. One indication that two peptide sequences are substantially identical is that one peptide is immunologically reactive with antibodies raised against the second peptide. Thus, a peptide is substantially identical to a second peptide, for example, where the two peptides differ only by a conservative substitution.

The term "identical" or "identity" in the context of two nucleic acid or peptide sequences refers to the residues in the two sequences which are the same when aligned for maximum correspondence over a specified comparison window. When percentage of sequence identity is used in reference to proteins or peptides it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., USA).

Methods of alignment of sequences for comparison are well-known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol.* 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene*, 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual alignment.

Isolated PKR peptide antagonists are no longer than 100 amino acid residues in length, preferably no more than 70, 60, or 50 amino acid residues in length, more preferably no more than 40, 35, or 30, amino acid residues in length, and most preferably no more than 25, 20, or 15 amino acid residues in length. PKR peptide antagonists may comprise amino acid residues which provide such useful physicochemical properties as aqueous solubility, hydrophobicity, and charge, or to confer epitopic sites, or additional biological activity to the PKR peptide antagonists. For example, PKR peptide antagonists of the invention may include cell-membrane permeable peptide sequences which provide for an increased rate of uptake from the extracellular medium. An exemplary cell-membrane permeable peptide has the sequence: AAVALLPAVLLALLAP (SEQ ID NO:19) (Lin et al., *J. Biol. Chem.* 270(2):14255–14258 (1995)); preferably, the cell-membrane permeable sequence is at the amino-terminus of the peptide. Thus, the present invention provides PKR peptide antagonists as: AAVALLPAVLLALLAPKGRSKQEAR (SEQ ID NO:20), and AAVALLPAVLLALLAPGRSKQEAR (SEQ ID NO:21).

Those of skill will recognize that PKR peptide antagonists that form a complex with regulatory RNA will preferably lack an high net negative charge which may destabilize the peptide antagonists interaction with the negatively charged regulatory RNA. Similarly, it will be understood that the PKR peptide antagonists will also preferably lack interfering amino acid sequences which reduce the ability of the peptide antagonist from forming a complex with regulatory RNA. Thus, for example, nuclear localization signal sequences, cytotoxic sequences, or sequences which sterically inhibit the formation of a regulatory RNA-peptide antagonist complex will preferably be absent from a PKR peptide antagonist of the present invention. The inability of a PKR peptide antagonist to form a complex with regulatory RNA can be assessed by any number of in vitro or in vivo methods as disclosed herein or known to those of skill in the art.

Amino acids of PKR peptide antagonists may also provide functional groups for linkage to: detectable labels, ligands to specifically deliver PKR peptide antagonists, or for linkage to therapeutic compositions. Detectable labels suitable for use in the present invention include any composition detectable by spectroscopic, photochemical, biochemical, radioisotopic, immunochemical, electrical, optical or chemical means and are discussed more fully, infra. Examples of ligands include, but are not limited to, antibodies, lymphokines, cytokines, receptor proteins such as CD4 and CD8, hormones, growth factors such as epidermal growth factor (EGF), and the like which specifically bind desired target cells. The term "specifically bind" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific binding, may be distinguished as mediated through specific recognition of the target molecule. Typically specific delivery results in a much stronger association between the ligand and cells bearing the ligand target molecule (i.e., receptor) than between the delivered molecule and cells lacking the target molecule. Specific binding typically results in greater than 2 fold, preferably greater than 5 fold, more preferably greater than 10 fold and most preferably greater than 100 fold increase in amount of bound molecule (per unit time) to a cell or tissue bearing the ligand target molecule as compared to a cell or tissue lacking the ligand target molecule.

Methods of covalent or non-covalent linkage of peptides to reporter molecules or ligands is well known in the art and will vary according to the chemical structure of the linked component. A "linker" as used herein refers to a molecule used to join, covalently or non-covalently, a PKR peptide antagonist to a chemical agent such as a diagnostic, prophylactic, or therapeutic compound to form a conjugate. Suitable linkers are well known to those of skill in the art and include, but are not limited to, straight or branched-chain carbon linkers, heterocyclic carbon linkers, or peptide linkers. See, e.g., Birch and Lennox, *Monoclonal Antibodies: Principles and Applications*, Chapter 4, Wiley-Liss, New York, N.Y. (1995); U.S. Pat Nos. 5,218,112, 5,090,914; Hermanson, *Bioconjugate Techniques*, Academic Press, San Diego, Calif. (1996). Where both molecules are peptides, the linkers may be joined to the constituent amino acids through their side groups (e.g., through a disulfide linkage to cysteine). A bifunctional linker having one functional group reactive with a group on a particular biologically active component, and another group reactive with a ligand, may be used to form the desired conjugate. Many procedures and linker molecules for attachment of various compounds to peptides are known. See, for example, European Patent Application No. 188,256; U.S. Pat. Nos.,4,671,958, 4,659, 839, 4,414,148, 4,699,784; 4,680,338; 4,569,789; and 4,589, 071.

It is sometimes desirable to release the conjugated molecule when it has reached a target site. Therefore, conjugates comprising linkages which are cleavable in the vicinity of the target site may be used. A number of different cleavable linkers are known to those of skill in the art. See U.S. Pat. Nos. 4,618,492; 4,542,225, and 4,625,014. U.S. Pat. No. 5,141,648 discloses immunoconjugates comprising linkers of specified chemical structure, wherein the linkage is cleaved in vivo thereby releasing the attached compound (radiotherapeutic agent, drug, toxin, etc.). The linker is susceptible to cleavage at a mildly acidic pH, and cleaved during transport into the cytoplasm of a target cell, thereby releasing the biologically active compound inside a target cell. U.S. Pat. No. 4,671,958 includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other components to peptides one skilled in the art will be able to determine a suitable method for attaching a given component to a PKR peptide antagonist of the present invention.

The PKR peptide antagonists of the invention and their conservatively modified variants form a complex with regulatory RNA such as, for example, HIV-1 TAR RNA. Formation of the complex can be determined by a variety of methods known to those of skill. Complex formation may be assessed by binding assays using regulatory RNA such as, but not limited to, poly-(rI)$_{50}$-poly-(rC)$_{50}$, where the percentage of peptide antagonist bound is quantified relative to the binding of poly(I)-poly(C) to PKR. See, e.g., Feng et al., *Proc. Natl. Acad. Sci.*, 89:5447–5451 (1992); Silverman et al., in *Lymphokines and Interferons: A Practical Approach*, eds. Clemens, M. J., Morris, A. G. & Gearing, A. J. H. (IRL, Washington), pp. 149–193 (1987). Complex formation by PKR peptide antagonists of the present invention yields values by binding assays of at least 15%, preferably at least 20% or 30%, and more preferably at least 40%, 50%, or 60% relative to wild-type PKR such as human PKR ("p68 kinase"). Alternatively, complex formation is determined by the ability of PKR peptide antagonists to inhibit PKR activation, as measured by reduction of PKR phosphorylation; or by the ability PKR peptide antagonists to inhibit eIF-2 alpha phosphorylation. Any inhibition assay known in the art can be used, and include for example, those described by Katze et al., *Mol. Cell. Biol.*, 11:5497–5505 (1991); Judware and Petryshyn, *Mol. Cell. Biol.*, 11:3259–3267 (1991); Barber et al., *Mol. and Cell. Biol.*, 15(6):3138–3146 (1995). PKR phosphorylation and/or eIF-2 alpha phosphorylation may each be reduced by PKR antagonists of the present invention by greater than 20%, 30%, 40%, 50%, or 60%.

Solid phase synthesis of PKR peptide antagonists in which the C-terminal amino acid of the sequence is attached to an insoluble support followed by sequential addition of the remaining amino acids in the sequence is the preferred method for the chemical synthesis of peptides of this invention. Techniques for solid phase synthesis are described by Barany and Merrifield, *Solid-Phase Peptide Synthesis*; pp. 3–284 in The *Peptides: Analysis, Synthesis, Biology*. Vol. 2: *Special Methods in Peptide Synthesis, Part A.*, Merrifield, et al. *J. Am. Chem. Soc.*, 85: 2149–2156 (1963), and Stewart et al., *Solid Phase Peptide Synthesis*, 2nd ed. Pierce Chem. Co., Rockford, Ill. (1984).

Nucleic Acids Encoding PKR Peptide Antagonists

The present invention provides nucleic acids of RNA, DNA, or chimeras thereof, which encode PKR peptide antagonists. Nucleic acids encoding PKR peptide antagonists can be made using standard recombinant or synthetic techniques. With the amino acid sequences of the PKR peptide antagonists herein provided, one of skill can readily construct a variety of clones containing functionally equivalent nucleic acids, such as nucleic acids which encode the same peptide. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Sambrook, et al., *Molecular Cloning: A Laboratory Manual* (2nd Ed., Vols. 1–3, Cold Spring Harbor Laboratory (1989)), *Methods in Enzymology*, Vol. 152: *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acid compositions of this invention, whether RNA, cDNA, genomic DNA, or a hybrid of the various combinations, are isolated from biological sources or synthesized in vitro. Deoxynucleotides may be synthesized chemically according to the solid phase phosphoramidite triester method described by Beaucage and Caruthers (1981), *Tetrahedron Letts.*, 22(20):1859–1862, e.g., using an automated synthesizer, e.g., as described in Needham-VanDevanter et al. (1984) *Nucleic Acids Res.*, 12:6159–6168.

Nucleic Acid Assays

The present invention further provides nucleic acid compositions and methods which are useful for the detection of nucleic acids in a biological sample which encode a mutation (e.g., substitutions, deletions, or additions) in human PKR. Thus, the present invention provides nucleic acids useful as probes. By "probes" or "nucleic acid probes" is meant nucleic acids which comprise a detectable label or which contain a functionality (e.g., biotin) which allow for binding of a detectable label. The nucleic acid probes selectively hybridize, under stringent conditions, to a nucleic acid encoding at least 5, more preferably 6 or 7, and most preferably at least 8, 9 or 10 contiguous amino acids at PKR amino acid positions 52–75, preferably 55–64, and most preferably at positions 57–64, or at positions 142–165, more preferably 145–154, most preferably 147–154, inclusive according to the numbering of Feng et al., *Proc. Natl. Acad. Sci. USA*, 89:5447–5451 (1992). Nucleic acids useful as probes are Y nucleotides in length where Y is an integer selected from the group consisting of from 18 to 50 nucleotides in length, inclusive. Preferably, nucleic acid probes are about any one of from 21 to 35 nucleotides in length. The nucleic acid sequence of human PKR is known. Feng et al., *Proc. Natl. Acad. Sci. USA*, 89:5447–5451 (1992); Meurs et al., *Cell*, 62:378–380 (1990). Thus, nucleic acids complementary to RNA or DNA sequences encoding the amino acids at the enumerated positions may readily be synthesized or, or alternatively a degenerate mixture of nucleic acids encoding at least 5 amino acids at the indicated positions can be synthesized.

The aforementioned amino acid subsequences of human PKR form a complex with regulatory RNA. Complex formation leads to PKR activation. Since inactive PKR is associated with malignant transformation of cells (Koromalis et al., *Science* 257:1685–1688 (1992)) the assays provided herein are useful in assaying human cells for nucleic acids encoding a variant of PKR which is unable to form a stable complex with regulatory RNA. Such assays aid in determining the molecular etiology of the tumor and assist the clinician in choosing a therapeutic regimen.

Alternatively, the nucleic acid assay can be used in an analysis of a family pedigree to determine predisposition to a malignancy due to expression of a mutant PKR in a diploid chromosomal complement. Methods of pedigree analysis using nucleic acid probes are known to those of skill in the art.

The method of detecting a mutation in a PKR peptide, comprises: (a) contacting a biological sample, under hybridization conditions, with a nucleic acid probe capable of selectively hybridizing to a PKR nucleic acid sequence to form a hybridization complex; and (b) detecting the formation of the hybridization complex as an indication of the presence or absence of a mutant PKR polynucleotide sequence in the sample. "Hybridization complex" refers to a duplex nucleic acid sequence formed by selective hybridization of two single-stranded nucleic acids with each other. The inability of nucleic acid probes of the present invention to selectively hybridize, under stringent hybridization conditions, with nucleic acids obtained from a biological sample of a tested individual indicates a sequence alteration (i.e., mutation) in the region of hybridization. By "selectively hybridizing" or "selective hybridization" is meant hybridization, under stringent hybridization conditions, of a nucleic acid sequence to a specified nucleic acid target sequence to a detectably greater degree than its hybridization to non-target nucleic acid sequences. Selectively hybridizing sequences have at least 80% sequence identity, preferably 90% sequence identity, and most preferably 100% sequence identity (i.e., complementary). By "biological sample" is meant a specimen comprising nucleic acids expressed by the chromosome complement of the tested individual. As used herein, "tested individual" refers to an individual, pre- or post-partum, alive or deceased, whose genome is being assayed for the presence of wild-type or mutant PKR. The biological sample may be a specimen of tumor cells from a tumorigenic growth, in which case a non-tumorigenic cell sample from the tested individual can be conveniently be used as a positive control in the assay.

"Stringent hybridization conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, N.Y. Generally, highly stringent conditions are selected to be about 5 degrees C lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ point for a particular probe. An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see Sambrook for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Methods of isolating total DNA or mRNA are well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993) and Chapt. 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993).

A variety of nucleic acid hybridization formats are known to those skilled in the art. For example, common formats include sandwich assays and competition or displacement assays. Hybridization techniques are generally described in Berger and Kimmel, (1987), supra.; "*Nucleic Acid Hybridization, A Practical Approach*" (Hames, B. D. and Higgins, S. J. (eds.), IRL Press, 1985; Gall and Pardue, (*Proc. Natl. Acad. Sci., U.S.A.* 63:378–383 (1969)); and John, Burnsteil and Jones (*Nature*, 223:582–587 (1969)).

For example, sandwich assays are commercially useful hybridization assays for detecting or isolating nucleic acid sequences. Such assays utilize a "capture" nucleic acid covalently immobilized to a solid support and a labeled "signal" nucleic acid in solution. The biological sample will provide the target nucleic acid. The "capture" nucleic acid probe and the "signal" nucleic acid probe hybridize with the target nucleic acid to form a "sandwich" hybridization complex. To be effective, the signal nucleic acid cannot hybridize with the capture nucleic acid.

In in situ hybridization, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4(3):230–250 (1986); Haase et al., *Methods in Virology*, Vol. VII, pp. 189–226 (1984); Wilkinson, "The theory and practice of in situ hybridization" In: *In situ Hybridization*, Ed. D. G. Wilkinson. IRL Press, Oxford University Press, Oxford; and *Nucleic Acid Hybridization: A Practical Approach*, Ed. Hames, B. D. and Higgins, S. J., IRL Press (1987).

Typically, labeled signal nucleic acids are used to detect hybridization. Complementary nucleic acids or signal nucleic acids may be labeled by any one of several methods typically used to detect the presence of hybridized oligonucleotides. The most common method of detection is the use of autoradiography with $^3$H, $^{125}$I, $^{35}$S, $^{14}$C, or $^{32}$P-labeled probes or the like. Other labels include ligands which bind to labeled antibodies, fluorophores, chemiluminescent agents, enzymes, and antibodies which can serve as specific binding pair members for a labeled ligand.

The label may also allow for the indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen, "Practice and Theory of Enzyme Immunoassays," *Laboratory Techniques in Biochemistry and Molecular Biology*" (Burdon, van Knippenberg (eds.), Elsevier, pp. 9–20 (1985)).

The detectable label used in nucleic acids of the present invention may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In another preferred embodiment, transcription amplification using a labeled nucleotide (e.g. fluorescein-labeled UTP and/or CTP) incorporates a label into the transcribed nucleic acids.

Alternatively, a label may be added directly to an original nucleic acid sample (e.g., mRNA, polyA MRNA, cDNA, etc.) or to the amplification product after the amplification is completed. Means of attaching labels to nucleic acids are well known to those of skill in the art and include, for example nick translation or end-labeling (e.g. with a labeled RNA) by phosphorylation of the nucleic acid and subsequent attachment (ligation) of a nucleic acid linker joining the sample nucleic acid to a label (e.g., a fluorophore).

Useful labels in the present invention include biotin for staining with labeled streptavidin conjugate, magnetic beads, fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The sensitivity of the hybridization assays may be enhanced through the use of a nucleic acid amplification system which multiplies a target nucleic acid being detected. The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including PCR®, LCR, QƎ-replicase amplification and other RNA polymerase mediated techniques (e.g., NASBA) are found in Berger, Sambrook, and Ausubel, as well as Mullis et al., (1987); U.S. Pat. No. 4,683,202; Arnheim & Levinson, *C&EN* 36–47 (1990); Lomell et al., *J. Clin. Chem.*, 35:1826 (1989); Van Brunt, *Biotechnology*, 8:291–294 (1990); Wu and Wallace, *Gene* 4:560 (1989); Sooknanan and Malek, *Biotechnology* 13:563–564 (1995); Innis; Kwoh; Guatelli; Landegren; and Barringer. Improved methods of cloning in vitro amplified nucleic acids are described in Wallace et al., U.S. Pat. No. 5,426,039. Other methods recently described in the art are the nucleic acid sequence based amplification (NASBA™, Cangene, Mississauga, Ontario) and Q Beta Replicase systems. These systems can be used to directly identify mutants where the PCR® or LCR primers are designed to be extended or ligated only when a select sequence is present. Alternatively, the select sequences can be generally amplified using, for example, nonspecific PCR® primers and the amplified target region later probed for a specific sequence indicative of a mutation.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

Kits

The nucleic acids of this invention can be included in a kit which can be used to rapidly determine the presence in a biological sample of PKR which is unable to form a complex with regulatory RNA. The kit typically includes a stable preparation of nucleic acids comprising a nucleic acid for performing the assay of the present invention. Further, the kit may also include a hybridization solution in either dry or liquid form for the hybridization of probes to target PKR nucleic acids, as well as a solution for washing and removing undesirable and non-hybridized nucleic acids, a substrate for detecting the hybridization complex, and instructions for performing and interpreting the assay.

Expression of Nucleic Acids

Once the nucleic acids encoding the PKR peptide antagonists of the present invention are isolated and cloned, one may express the desired polypeptides in a recombinantly engineered cell such as bacteria, yeast, insect (especially employing baculoviral vectors), plant and mammalian cells. It is expected that those of skill in the art are knowledgeable in the numerous expression systems available for expression of the DNA encoding the PKR peptide antagonists. No attempt to describe in detail the various methods known for the expression of peptides in prokaryotes or eukaryotes will be made.

In brief summary, the expression of natural or synthetic nucleic acids encoding PKR peptide antagonists will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the PKR peptide antagonists. To obtain high level expression of a cloned gene, it is desirable to construct expression plasmids which contain, at the minimum, a strong promoter to direct transcription, a ribosome binding site for translational initiation, and a transcription/translation terminator.

In construction of recombinant expression cassettes of the invention (to express PKR antagonists), a promoter fragment, either related to the PKR antagonists of this invention or heterologous to the PKR antagonists, may be employed which will direct expression of the gene in all tissues of a transgenic organism. Such promoters are referred to herein as "constitutive" promoters and are active under most environmental conditions and states of development or cell differentiation. Examples of constitutive promoters of plants include the cauliflower mosaic virus (CaMV) 35S transcription initiation region, the 1'- or 2'-promoter derived from T-DNA of *Agrobacterium tumafaciens*, promoter of the tobacco mosaic virus and transcription initiation regions from various plant genes known to those of skill in the art.

Alternatively, the promoter may direct expression of the polynucleotide of the invention in a specific tissue (tissue-specific promoters) or may be otherwise under more precise environmental control (inducible promoters). Examples of tissue-specific plant promoters under developmental control include promoters that initiate transcription only in certain tissues, such as fruit, seeds, or flowers. The tissue specific E8 promoter from tomato is particularly useful for directing gene expression so that a desired gene product is located in fruits. Other suitable promoters include those from genes encoding embryonic storage proteins. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on transformed cells. For example, the marker may encode antibiotic resistance, particularly resistance to kanamycin, G418, bleomycin and hygromycin.

Plants can be transformed using viral vectors, such as, for example, the tobacco mosaic virus, to express PKR antagonists of the invention. Selection and construction of vectors and techniques for transforming a wide variety of plant cells are well known, for example, see Hamamoto, et al., U.S. Pat. No. 5,618,699.

One of skill would recognize that modifications can be made to PKR peptide antagonists without diminishing their biological activity. Some modifications may be made to facilitate the cloning, expression, or incorporation of the targeting molecule into a fusion protein or peptide. Such modifications are well known to those of skill in the art and include, for example, a methionine added at the amino terminus to provide an initiation site, or additional amino acids (e.g., poly His) placed on either terminus to create conveniently located restriction sites or termination codons or epitopes to facilitate purification and/or detection. Such modification can be made to make a peptide easily (more) detectable, e.g., by incorporating a radio-label into the peptide, and used to detect antibodies specifically reactive with the peptide. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance or impact on other useful or desired properties.

The antagonist proteins of the invention can also be expressed as recombinant proteins with one or more additional polypeptide domains added to facilitate protein purification. Such purification facilitating domains include, but are not limited to, metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the purification domain and PKR antagonist is useful to facilitate purification. One such expression vector provides for expression of a fusion protein comprising the sequence encoding PKR antagonist and nucleic acid sequence encoding six histidine residues followed by thioredoxin and an enterokinase cleavage site. The histidine residues facilitate purification while the enterokinase cleavage site provides a means for purifying the PKR antagonist protein(s) from the fusion protein. The technology and literature pertaining to vectors containing fusion proteins is well-known and available in the art (See e.g., Kroll et al., (1993) DNA Cell. Biol., 12:441–53).

1. Expression in Prokaryotes

Examples of regulatory regions suitable for this purpose in *E. coli* are the promoter and operator region of the *E. coli* tryptophan biosynthetic pathway as described by Yanofsky, Bacteriol. 158:1018–1024 (1984), and the leftward promoter of phage lambda $P_L$) as described by Herskowitz and Hagen, *Ann. Rev. Genet.*, 14:399–445 (1980). The inclusion of selection markers in DNA vectors transformed in *E. coli* is also useful. Examples of such markers include genes specifying resistance to ampicillin, tetracycline, or chloramphenicol. See, Sambrook, et al. for details concerning selection markers for use in *E. coli*.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing PKR peptide antagonists are available using *E. coli*, Bacillus sp. and Salmonella (Palva, et al., *Gene* 22:229–235 (1983); Mosbach, et al., *Nature* 302:543–545 (1983).

When expressing-the PKR peptide antagonists in *S. typhimurium*, one should be aware of the inherent instability of plasmid vectors. To circumvent this, the foreign gene can be incorporated into a nonessential region of the host chromosome. This is achieved by first inserting the gene into a plasmid such that it is flanked by regions of DNA homologous to the insertion site in the Salmonella chromosome. After introduction of the plasmid into the *S. typhimurium*, the foreign gene is incorporated into the chromosome by homologous recombination between the flanking sequences and chromosomal DNA.

An example of how this can be achieved is based on the his operon of Salmonella. Two steps are involved in this process. First, a segment of the his operon must be deleted in the Salmonella strain selected as the carrier. Second, a plasmid carrying the deleted his region downstream of the gene encoding the PKR peptide antagonists is transformed into the his Salmonella strain. Integration of both the his sequences and a gene encoding a PKR peptide antagonist occurs, resulting in recombinant strains which can be selected as $his^+$.

Bacterial strains which can be used to express exogenous nucleic acid include, for example, *Escherichia coli, Streptococcus cremoris, Streptococcus lactis, Streptococcus thermophilus, Leuconostoc citrovorum, Leuconostoc mesenteroides, Lactobacillus acidophilus, Lactobacillus lactis, Bifidobacterium bifidum, Bifidobacteriu breve*, and *Bifidobacterium longum.*

Detection of the expressed peptide is achieved by methods known in the art and include, for example, radioimmunoassays, Western blotting techniques or immunoprecipitation. Purification from *E. coli* can be achieved following procedures described in U.S. Pat. No. 4,511,503.

2. Expression in Eukaryotes.

A variety of eukaryotic expression systems such as yeast, insect cell lines, bird, fish, and mammalian cells, are known to those of skill in the art. As explained briefly below, PKR peptide antagonists of the present invention may be expressed in these eukaryotic systems.

Synthesis of heterologous proteins or peptides in yeast is well known. *Methods in Yeast Genetics*, Sherman, F., et al., Cold Spring Harbor Laboratory, (1982) is a well recognized work describing the various methods available to produce the peptide in yeast. Yeast strains which can be used to express exogenous nucleic acid include *Pichia 1196 pastoris, Torulopsis holmil, Saccharomyces fragilis, Saccharomyces cerevisiae, Saccharomyces lactis*, and *Candida pseudotropicalis.*

Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., 1979*, Gene*, 8:17–24; Broach, et al., 1979*, Gene*, 8:121–133).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, 1978*, Nature* (London), 275:104–109; and Hinnen, A., et al., 1978*, Proc. Natl. Acad. Sci. USA*, 75:1929–1933. The second procedure does not involve removal of the cell wall. Instead the cells are treated with lithium chloride or acetate and PEG and put on selective plates (Ito, H., et al., 1983*, J. Bact*., 153:163–168).

PKR peptide antagonists, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding PKR peptide antagonists can also be ligated to various expression vectors for use in transforming cell cultures of, for instance, mammalian, insect, bird or fish origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells, etc. Expression vectors for these cells can include expression control sequences, such as an origin of replication, a promoter (e.g., the CMV promoter, a HSV tk promoter or pgk (phosphoglycerate kinase) promoter), an enhancer (Queen et al. (1986) *Immunol. Rev*. 89:49), and necessary processing information sites, such as ribosome binding sites, RNA splice sites, polyadenylation sites (e.g., an SV40 large T Ag poly A addition site), and transcriptional terminator sequences. Other animal cells useful for production of PKR peptide antagonists are available, for instance, from the American Type Culture Collection Catalogue of Cell Lines and Hybridomas (7th edition, 1992).

Appropriate vectors for expressing PKR peptide antagonists in insect cells are usually derived from the SF9 baculovirus. Suitable insect cell lines include mosquito larvae, silkworm, armyworm, moth and Drosophila cell lines such as a Schneider cell line (See Schneider *J. Embryol. Exp. Morphol*. 27:353–365 (1987).

As indicated above, the vector, e.g., a plasmid, which is used to transform the host cell, preferably contains DNA sequences to initiate transcription and sequences to control the translation of the peptide. These sequences are referred to as expression control sequences.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., 1983*, J. Virol*. 45: 773–781).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in *DNA Cloning Vol. II a Practical Approach* Ed. D. M. Glover, IRL Press, Arlington, Va. pp. 213–238.

The host cells are competent or rendered competent for transformation by various means. There are several well-known methods of introducing DNA into animal cells. These include: calcium phosphate precipitation, fusion of the recipient cells with bacterial protoplasts containing-the DNA, treatment of the recipient cells with liposomes containing the DNA, DEAE dextran, electroporation and micro-injection of the DNA directly into the cells.

The transformed cells are cultured by means well known in the art. *Biochemical Methods in Cell Culture and Virology*, Kuchler, R. J., Dowden, Hutchinson and Ross, Inc., (1977). The expressed polypeptides are isolated from cells grown as suspensions or as monolayers. The latter are recovered by well known mechanical, chemical or enzymatic means.

Purification of Expressed Peptides

The PKR peptide antagonists of the present invention which are produced by recombinant DNA technology may be purified by standard techniques well known to those of skill in the art. Recombinantly produced PKR peptide antagonists can be directly expressed or expressed as a fusion protein or peptide. The phrase "recombinant peptide" or "recombinantly produced peptide" refers to a peptide produced using non-native cells that do not have an endogenous copy of DNA able to express the peptide. The cells produce the peptide because they have been genetically altered by the introduction of the appropriate nucleic acid sequence. The recombinant peptide will not be found in association with proteins, peptides, and other subcellular components normally associated with the cells producing the peptide. The peptide can then purified by a combination of cell lysis (e.g., sonication) and affinity chromatography. For fusion products, subsequent digestion of the fusion peptide with an appropriate proteolytic enzyme releases the desired peptide.

The peptides of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982); Deutscher, Guide to Protein Purification, Academic Press, 1990. For example, antibodies may be raised to the PKR peptide antagonists as described herein. Cell lysates are prepared by standard methods and the peptide extracted by immunoprecipitation. The peptide may then be further purified by standard protein chemistry techniques as described above.

Antibodies and Antibody Production

The present invention further provides antibodies to the PKR peptide antagonists of the present invention. The term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. Antibodies exist e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, *Fundamental Immunology*, Third Edition, W. E. Paul, ed., Raven Press, N.Y. 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

Antibodies are raised to the PKR peptide antagonists of the present invention, including individual, allelic, strain, or species variants, and fragments thereof, both in their naturally occurring (full-length) forms and in recombinant forms. Additionally, antibodies are raised to these peptide antagonists in either their native configurations or in non-native configurations. Anti-idiotypic antibodies can also be generated. Antibodies raised to a PKR peptide antagonist is specifically immunoreactive with the PKR peptide antagonist. The phrase "specifically immunoreactive with", when referring to an antibody refers to a binding reaction which is determinative of the presence of the peptide antagonist in the presence of a heterogeneous population of proteins and other biologics. Thus, under designated immunoassay conditions, the specified antibodies bind preferentially to a particular PKR peptide antagonist and do not bind in a significant amount to other proteins or peptides present in the sample. Specific binding to a peptide antagonist under such conditions requires an antibody that is selected for its specificity for a particular protein or peptide. A variety of immunoassay formats may be used to select antibodies specifically immunoreactive with a particular protein or peptide. For example, solid-phase ELISA immunoassays are routinely used to select monoclonal antibodies specifically immunoreactive with a peptide. See Harlow and Lane (1988) Antibodies, A Laboratory Manual, Cold Spring Harbor Publications, New York, for a description of immunoassay formats and conditions that can be used to determine specific immunoreactivity.

Many methods of making antibodies are known to persons of skill. The following discussion is presented as a general overview of the techniques available; however, one of skill will recognize that many variations upon the following methods are known.

A number of immunogens are used to produce antibodies specifically reactive with PKR peptide antagonists. Recombinant or synthetic peptides of seven amino acids in length, or greater, selected from amino acid subsequences of each of the sequences selected from the group consisting of SEQ ID NOS: 1 through 6, are the preferred peptide immunogen (antigen) for the production of monoclonal or polyclonal antibodies. The term "subsequence" in the context of a particular nucleic acid or peptide sequence refers to a region of the nucleic acid or peptide equal to or smaller than the particular nucleic acid or peptide. In one class of preferred embodiments, an immunogenic peptide conjugate is also included as an immunogen. Naturally occurring peptides are also used either in pure or impure form.

Antibodies reactive with these PKR immunogens bind to the double-stranded (ds) (regulatory) RNA binding site of PKR and inhibit the ability of PKR to bind, and be activated by, dsRNA (the "regulatory RNA). Thus, in one embodiment of the invention, antibodies specifically reactive with PKR peptide antagonists are used in a method of antagonizing regulatory RNA binding to double-stranded RNA dependent protein kinase (PKR). In another embodiment, the invention includes the method of claim 34, where the method comprises contacting the antibody with a PKR within a eukaryotic cell.

Recombinant PKR peptide antagonists are expressed in eukaryotic or prokaryotic cells and purified using standard techniques. The PKR peptide antagonist, or a synthetic version thereof, is then injected into an animal capable of producing antibodies. Either monoclonal or polyclonal antibodies can be generated for subsequent use in immunoassays to measure the presence and quantity of the peptide antagonist.

Methods of producing polyclonal antibodies are known to those of skill in the art. In brief, an immunogen (antigen), preferably a purified peptide, a peptide coupled to an appropriate carrier (e.g., GST, keyhole limpet hemanocyanin, etc.), or a peptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the PKR peptide antagonist of interest. When appropriately high titers of antibody to the immunogen are obtained, blood is collected from the animal and antisera are prepared. Further fractionation of the antisera to enrich for antibodies reactive to the peptide antagonist is performed where desired (see, e.g., Coligan (1991) *Current Protocols in Immunology* Wiley/Greene, N.Y.; and Harlow and Lane (1989) *Antibodies: A Laboratory Manual* Cold Spring Harbor Press, N.Y.).

Antibodies, including binding fragments and single chain recombinant versions thereof, against PKR peptide antagonists are raised by immunizing animals, e.g., with conjugates of the fragments with carrier proteins as described above. Typically, the immunogen of interest is a peptide of at least about 4 amino acids, more typically the peptide is 10 amino acids in length, preferably, the fragment is 15 amino acids in length and more preferably the fragment is 20 amino acids in length or greater. The peptides are typically coupled to a carrier protein (e.g., as a fusion protein), or are recombinantly expressed in an immunization vector. Antigenic determinants on peptides to which antibodies bind are typically 4 to 10 amino acids in length.

Monoclonal antibodies are prepared from cells secreting the desired antibody. These antibodies are screened for binding to normal or modified peptides, or screened for agonistic or antagonistic activity. Specific monoclonal and polyclonal antibodies will usually bind with a $K_D$ of at least about 0.1 mM, more usually at least about 50 $\mu$M, and most preferably at least about 1 $\mu$M or better.

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The PKR peptide antagonists and antibodies of the present invention are used with or without modification, and include chimeric antibodies such as humanized murine antibodies.

Other suitable techniques involve selection of libraries of recombinant antibodies in phage or similar vectors (see, e.g., Huse et al. (1989) *Science* 246:1275–1281; and Ward, et al. (1989) *Nature* 341:544–546; and Vaughan et al. (1996) *Nature Biotechnology*, 14:309–314).

Frequently, the peptide antagonists and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l. Acad. Sci. USA* 86: 10029–10033.

Methods of Antagonizing Binding

The present invention also provides methods of antagonizing the binding of regulatory RNA to PKR. The method comprises contacting a PKR peptide antagonist with regulatory RNA to form a regulatory RNA-antagonist complex. The structure of PKR peptide antagonists of the present invention is more fully discussed, supra. The regulatory RNA can be any one of the RNA molecules selected from the group consisting of: poly-riboinosine (50 bases long) :poly-ribocytosine (50 bases long), reovirus dsRNA, and HIV-1 TAR RNA. Other regulatory RNA molecules can be readily identified by their ability to form a stable complex with PKR as determined using the eIF-2 alpha phosphorylation or PKR phosphorylation assays discussed, supra.

Contacting the regulatory RNA with the PKR peptide antagonists of the present invention occurs under physiological conditions. "Physiological conditions" as used herein to refer to conditions (e.g., temperature, osmolarity, pH) that are typical inside a living organism or a cell. While it is recognized that some organs are subject to extreme conditions, the intra-organismal and intra-cellular environment normally varies around pH 7 (i.e. from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The procedure of contacting may occur in eukaryotic cells such as mammalian cells. Mammalian cells employed in the present invention include rat, murine, porcine, canine, bovine, or human cells. Cells may be contacted with PKR peptide antagonists in cell culture, within the host organism (i.e., in vivo) or contacted outside the body of the host (i.e., ex vivo) and subsequently reintroduced into the host organism. Alternatively, PKR peptide antagonists can be contacted with regulatory RNA in cell free systems including cellular lysates.

Exogenously synthesized PKR peptide antagonists may be added directly to the cell or cell-free system comprising regulatory RNA, or may be synthesized de novo within the cell from a nucleic acid encoding PKR peptide antagonists. Methods of introducing peptides into cells is well known in the art and include the use of colloidal carriers such as proteinoids, microemulsions, and liposomes. WO 90/03164; WO 91/14454; WO 92/18147; U.S. Pat. Nos. 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496. Other types of microparticulate drug delivery systems are known such as microspheres (WO 93/00077), liposheres (U.S. Pat. No. 5,188,837), microcapsules (EP 442671), or other lipid vesicles (Yoshida et al., EPA 140,085). Surfactants of many types have been utilized as promoters of peptide absorption (EP 115627; GB 2,127,689; and U.S. Pat. No. 4,548,922).

A large number of nucleic acid delivery methods are well known to those of skill in the art. Such methods include, for example liposome-based gene delivery (Debs and Zhu (1993) WO 93/24640; Mannino and Gould-Fogerite (1988) *BioTechniques* 6(7): 682–691; Rose U.S. Pat No. 5,279,833; Brigham (1991) WO 91/06309; Felgner et al. (1987) *Proc. Natl. Acad. Sci. USA* 84: 7413–7414; Budker et al., *Nature Biotechnology*, 14(6):760–764 (1996)), and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res*. 4:43, and Cornetta et al. *Hum. Gene Ther*. 2:215 (1991)). Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) *J. Virol*. 66(5) 2731–2739; Johann et al. (1992) *J. Virol*. 66 (5):1635–1640 (1992); Sommerfelt et al., (1990) *Virol*. 176:58–59; Wilson et al. (1989) *J. Virol*. 63:2374–2378; Miller et al., *J. Virol*. 65:2220–2224 (1991); Wong-Staal et al., PCT/US94/05700, and Rosenburg and Fauci (1993) in *Fundamental Immunology*, Third Edition Paul (ed) Raven Press, Ltd., New York and the references therein, and Yu et al., *Gene Therapy* (1994) supra). Other methods known to the skilled artisan include electroporation, direct gene transfer, particle bombardment, and receptor-mediated uptake.

Therapeutic Compositions and Pharmacological Applications of PKR Peptide Antagonists The PKR peptide antagonists of the present invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the PKR peptide antagonists, when administered orally, must be protected from digestion. This is typically accomplished either by complexing the peptide with a composition to render it resistant to acidic and enzymatic hydrolysis or by packaging the peptide in an appropriately resistant carrier such as a liposome. Means of protecting proteins or peptides from digestion are well known in the art.

The pharmaceutical compositions of this invention are particularly useful for topical administration to stimulate wound healing. In another embodiment, the compositions are useful for parenteral administration, such as intravenous administration or administration into a body cavity or lumen of an organ. The compositions for administration will commonly comprise a solution of the PKR peptide antagonists dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient of an average body weight of 70 Kg per day. Dosages up to about 1000 mg per patient of an average body weight of 70 Kg per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science*, 19th ed., Mack Publishing Company, Easton, Pa. (1995).

Formulations suitable for parenteral administration, such as, for example, by intra-articular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration.

The compositions-containing the present PKR peptide antagonist can be administered for therapeutic treatments. In therapeutic applications, compositions are administered to a patient suffering from a disease or injury in an amount sufficient to cure or at least partially arrest the disease or injury and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the peptides of this invention to effectively treat the patient.

Protection of PKR peptide pharmaceuticals from protease activity is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The PKR peptide antagonists can be targeted and protected by liposomes that bear immunoglobulins or ligands that are specific for specific cells. For example if a T cell were the selected target cell, typical membrane receptor/targets would include CD2 (T11), CD3, CD4 and CD8. If B cells were the target cells, subcellular targets might include CD10 (CALLA antigen), CD19 and CD20. CD45 is a possible target that occurs broadly on lymphoid cells. Those skilled in the art will realize that other ligand effectors may be chosen that bind to receptors expressed on still other types of cells as described above, for example, membrane glycoproteins or ligand or hormone receptors such as epidermal growth factor receptor and the like.

Among various uses of the PKR peptide antagonists of the present invention are included a variety of conditions in which cell proliferation is desirable, such as triggering self-replication and expansion of hematopoietic and other stem cells, stimulating bone replacement following fracture, osteoporosis or arthritis, promoting regeneration of cells otherwise difficult to proliferate (e.g., muscle, nerve), treating sickle cell disease by stimulating fetal-hemoglobin producing cells, restoring T cell populations in immune compromised patients, and inhibiting TAR RNA activation of PKR in HIV-1 infected individuals. The pharmaceutical compositions are useful for both medical and veterinary applications in the treatment of mammals, particularly humans.

Anti-cytotoxic, Cell-protective Effect of PKR Antagonists

In another embodiment of the invention, PKR antagonists are administered to AIDS patients to exert an anti-cytotoxic and cell-protective effect. In a further embodiment of the invention, this cell-protective effect extends to the inhibition of apoptosis by the administration of the invention's PKR antagonists. When administered to HIV-1-infected lymphocytes (e.g., as used in this Example, human lymphoblastoid cell line MT-4, described in Susloparov, et al., *Mol. Gen. Mikrobiol. Virusol.* 2, 32–39 (1996) ), the cell-permeable PKR peptide antagonist comprising SEQ ID NO:31 protected the cells against cell lysis (and death) and promoted the expression of CD4+ cells amongst the surviving cells (as described in Example 7). The PKR antagonist can be increasing expression of CD4 or it can be maintaining the expression of CD4 on the cell surface of the lymphoblastoid cells. The therapeutic benefit of such an administration is beneficial in maintaining the immune system of patients suffering from HIV-1 infection, as HIV-1 pathogenesis is characterized by loss of CD4 positive cells.

Administration of the PKR antagonists of the invention is also used as a cell-protective agent. The PKR antagonist can be protecting the cell against death by blocking the apoptosis pathway. The apoptosis pathway has been shown to be triggered by transfection and expression of recombinant, wild-type PKR. Lee, et al., *Virology* 199:491–496 (1994). However, apoptosis is not triggered by a mutant PKR which lacked the third basic amino acid region, Lee, et al. *Virology* 231:81–88 (1997). Furthermore, expression of the human proto-oncogene bcl-2 blocks PKR-induced apoptosis, but not PKR-induced inhibition of translation. Lee, et al., Ibid. After administration of PKR antisense expression vector to promonocytic U937 cells, the cells became resistant to tumor necrosis factor (TNF)-alpha-induced apoptosis. Yeung, et al., *Proc. Natl. Acad. Sci. USA* 93:12451–12455 (1996). PKR antagonists can be exhibiting their cell-protective, anti-lytic effect by independent mechanisms: one mediated by inhibition of translation mechanisms, and the other through inhibition of programmed cell death, i.e., apoptosis. Thus, in one embodiment, the PKR antagonists of the invention are administered to inhibit the process of programed cell death, or apoptosis.

Methods of Demonstrating the Apoptosis-Inhibiting Effect of PKR Antagonists

In a further embodiment of the invention, the PKR antagonists of the invention have a cell-protective effect by through their ability to inhibit apoptosis. Apoptosis can be measured by a variety of techniques. For example, apoptosis can be measured by determination of cell phenotype. Phenotype refers to how the cell looks, typically microscopically, but gross or macroscopic appearance can be observed. The phenotype changes depending on the growth rate of the cells. For instance, the microscopic morphology of cells that are rapidly dividing and growing is different than that of cells undergoing cell death by apoptosis. Determination of cell phenotype is well within the ability of one with ordinary skill in the art.

There are also a number of biochemical assays that can be used to detect apoptosis, such as "laddering" of the cellular DNA. When testing compounds for the ability to induce apoptosis, cell death (not cytostasis) is an endpoint of compound application to the cell. A classic signature of apoptosis is the cleavage of nuclear DNA into nucleosomal subunits. On gels, this gives rise to the appearance of a ladder as nucleosomal units are sequentially cleaved from the DNA. Observation of a classic DNA ladder is indicative of apoptosis. For example, cells are lysed and the high molecular DNA is removed by centrifugation. The aqueous phase is treated with proteinase K to digest proteins. After a phenol/chloroform extraction, the DNA is precipitated with salt and ethanol. The pellet is dissolved in deionized water and treated with 500 µg/ml RNase A. The DNA is run on a 2% agarose minigel. Observation for a classic DNA ladders is made. A gel photograph can be taken. Cell death is verified by the demonstration of DNA fragmentation as represented by the ladder configurations on the gel. (See Gavrieli, Y., et al. (1992) *J. Cell Biol.* 119:493). There are also a variety of other assays available for apoptosis such as "TUNEL" assays (see White, E., et al. (1984) *J. Virol.* 52:410).

Although the present invention has been described in some detail by way of illustration and example for purposes of clarity of understanding, it will be obvious that certain changes and modifications may be practiced within the scope of the appended claims.

EXAMPLE 1

Example 1 describes the effect of PKR peptide antagonists on the phosphorylation of PKR.

{gamma-$^{32}$P} ATP (3000 Ci/mmol) were obtained from Amersham. The eIF-2 alpha and PKR from rabbit reticulocytes were purified as described, Andrews, et al., *J. Biol. Chem.* 260:7628–7635 (1985) and Petryshyn, et al., *Methods Enzymol.* 99:346–362 (1983), respectively. Heme-regulated kinase (HRI) was purified as described in Trachsel, et al., *Proc. Natl. Acad. Sci. USA*. 75:3654–3658 (1978). Plasmid pSP64TAR-CAT is described in Parkin, et al., *EMBO J.* 7:2831–2837 (1988).

Peptide synthesis: Peptides were generated by automated Fmoc solid phase synthesis using Applied Biosystems Model 431 running in small-scale "Fastmoc" mode. Synthetic peptides were cleaved from the solid support using a TFA-based method (King, et al., Int. *J. Peptide Prot. Res.* 36:255–256 (1990)) followed by ether or ethyl acetate precipitation, centrifugation, and vacuum desiccation. All reagents for synthesis and cleavage were HPLC grade.

Relative peptide purity was assessed by reverse phase C-18 HPLC and was typically approximately 80%. Composition was routinely verified by mass spectrometry. R1-peptide (AKGRSKQEARNAAAKLAVDIL (SEQ ID NO:13)) corresponds to residues 54–74 of murine PKR. hR1 peptide (residues KKEAKNAAAKLAVEILNKEKK (SEQ ID NO:15)) corresponds to resides 60–80 of human PKR. Peptide 271 (DMLPKKSEESAAPSR (SEQ ID NO:22)) and peptide 273 (SSAARPSGRRRDPAG (SEQ ID NO:23)), were selected for similarity of reverse-phase chromatographic properties and composition to the R1-peptide. Peptide 274 (KGSKNALAARVIAAQRELKD (SEQ ID NO:24) was synthesized as a random R1 peptide.

Transcription of TAR RNA. Plasmid pSP64 TAR-CAT containing a cDNA for TAR RNA (nucleotides +1 to +82 of the HIV-1 LTR) was linearized by HindIII and used as a template. Transcription reactions were performed as recommended by Ambion, and contained Ambion transcription buffer, 7.5 mM of each GTP, ATP, UTP and CTP, 1 $\mu$g of linearized plasmid and Ambion enzyme mix containing SP6 polymerase. To trace label TAR RNA, the same reaction was performed except that 10–20 $\mu$Ci of [alpha-$^{32}$P] CTP (3000 Ci/mmol) was added.

Protein kinase assays containing 4–5 ng of purified PKR from rabbit reticulocytes were performed with the indicated amounts of dsRNA in a buffer containing 10 mM Tris-HCl (7.8), 2 mM Mg(OAc)$_2$, 50 mM KCl at 30EC. The reaction volumes were 20 $\mu$l. After 10 min of incubation the reactions were stopped by addition of 7 $\mu$l 4×SDS loading/denaturing buffer. The samples were subjected to SDS-7.5% polyacrylamide gel electrophoresis and autoradiography [Ernst, et al., *J. Biol. Chem.* 53:7163–7172 (1978)]. Kinase assays for HRI were essentially the same except purified HRI was used.

RNA mobility-shift assays were performed as described elsewhere [Judware, et al., *J. Interferon Res.* 13:153–160 (1993)]. Briefly, 50 ng of $^{32}$P-labeled TAR RNA (approx. 3×105 cpm/$\mu$g) was incubated in the presence of 5 ng of PKR under conditions for the kinase assay. Complexes were resolved utilizing 5% or 10% nondenaturing polyacrylamide gels. Mobility shift assays with the use of peptides were essentially the same except SDS (2%) were added to some reactions before application to a gel. To determine the relative amounts of phosphorylated PKR and eIF-2 alpha, corresponding bands on autoradiograms were quantitated by scanning densitometry.

Synthetic peptides with identical sequences to the R1 (SEQ ID NO:13) and hR1 (SEQ ID NO:1 5) regions were prepared and utilized to directly assess their role in PKR activation. The studies were carried out utilizing both a synthetic dsRNA (poly(I)-poly(C)) and the 83-nucleotide long TAR RNA found in the 5' region of all HIV-I mRNAs. The phosphorylation of PKR can be seen with as little as 200 ng/ml and increased as the concentration of TAR RNA was elevated to 2 $\mu$g/ml, the highest concentration tested. No phosphorylation of PKR was observed in the absence of dsRNA. The phosphorylation of PKR by poly(I)-poly(C) can be seen with as little as 1 ng/ml and reaches a maximum level between 45–200 ng/ml poly(I)-poly(C). TAR RNA also facilitated the phosphorylation of PKR in a concentration dependent manner, however, higher concentrations were needed for efficient phosphorylation. The phosphorylation of PKR could be seen with as little as 200 ng/ml and increased as the concentration of TAR RNA was elevated to 2 $\mu$g/ml, the highest concentration tested. The higher levels of TAR RNA needed for phosphorylation of PKR are expected because of its lower intrinsic dsRNA content relative to poly(I)-poly(C), and is consistent with other studies (Edery, et al., *Cell* 56:303–312 (1989); Roy, et al., *J. Virol.* 2 65:632–640 (1991); Judware, et al., *J. Interferon Res.* 13:153–160 (1993); Maitra, et al., *Virology* 204:823–827 (1994)).

In subsequent experiments, we used 45 ng/ml poly(I)-poly(C) and 2 $\mu$g/ml TAR RNA for assays. The addition of R1-peptide (SEQ ID NO:13) to kinase reactions containing TAR RNA resulted in an inhibition of PKR phosphorylation. Quantitation of autoradiograms indicated that as little as 80 $\mu$M of R1-peptide (SEQ ID NO:13) resulted in 50% reduction in PKR phosphorylation and complete inhibition was observed at 400 $\mu$M. Similarly, the hR1 peptide (SEQ ID NO:15) to kinase reaction containing TAR RNA resulted in 80% inhibition at 375 $\mu$M while 50% inhibition was observed at 150 $\mu$M hR1 peptide (SEQ ID NO:15). Moreover, the R1-peptide (80 $\mu$M) (SEQ ID NO:13) and hR1 (375 $\mu$M)(SEQ ID NO:15) peptides efficiently prevented the phosphorylation of PKR in the presence of poly(I)-poly(C) (75% inhibition). Thus the R1 and hR1 peptides were effective in blocking the phosphorylation of PKR by both TAR RNA and poly(I)-poly(C).

EXAMPLE 2

Example 2 describes the effect of PKR peptide antagonists on the phosphorylation of eIF-2 alpha.

PKR, once phosphorylated, becomes converted to an active enzyme which phosphorylates the alpha-subunit of eIF-2 (eIF-2 alpha). The effect of the R1-peptide (SEQ ID NO:13) on the phosphorylation of this physiologic substrate was examined. Concomitant with the inhibition in phosphorylation of PKR, the R1-peptide (80 $\mu$M)(SEQ ID NO:13) prevented the phosphorylation of eIF-2 alpha (75% inhibition). The loss of eIF-2 alpha phosphorylation appears largely due to a direct effect on PKR activation, because the addition of R1-peptide (80 $\mu$M) (SEQ ID NO:13) after the kinase had already undergone subsequent phosphorylation and activation, had no effect on the phosphorylation of eIF-2 alpha. However, at high levels of R1-peptide (400 $\mu$M)(SEQ ID NO:13), some inhibition of eIF-2 alpha phosphorylation was observed in the presence of phosphorylated PKR. In addition to PKR and eIF-2 alpha several other phosphoprotein bands were observed which represent contaminating phosphoproteins present in the eIF-2 alpha preparation. These phosphoproteins were observed in the absence of dsRNA and were largely unaffected by dsRNA or the R1-peptide (SEQ ID NO:13). This suggests that the R1-peptide (SEQ ID NO:13) is not a non-specific inhibitor of protein phosphorylation. This is further supported by the observation that the R1-peptide (400 $\mu$M)(SEQ ID NO:13) had little or no effect on either the autophosphorylation of the heme-regulated kinase (HRI) or its substrate, which is also eIF-2 alpha. Thus at low levels, the R1-peptide (SEQ ID NO:13) prevents the autophosphorylation and activation of PKR but has little effect once the kinase has been activated.

EXAMPLE 3

Example 3 describes the effect of PKR peptide antagonists on the binding of TAR RNA to PKR.

The interaction of PKR with TAR RNA has been successfully studied using RNA mobility-shift analysis [Edery, et al, *Cell* 56:303–312 (1989); Roy, et al., *J. Virol* 65:632–640 (1991); Judware, et al., *J. Interferon Res.* 13:153–160 (1993); Maitra, et al., *Virology* 204:823–827

(1994)]. This method was utilized to examine the effect of R1-peptide (SEQ ID NO:13) on the binding of PKR to TAR RNA. RNA mobility-shift assays containing only highly purified PKR (5 ng) and radio-labeled TAR gave rise to a prominent slowly migrating RNA-protein complex when separated on either 5% or 10% polyacrylamide gels. This complex appeared to be the result of a specific interaction Table 1 shows a sequence alignment of PKR from the indicated species and TAR RNA binding protein (Gatignol et al., *Mol. Cell. Biol.*, 13:2193–2202 (1993)). Table 1 also shows a consensus PKR sequence. PKR was numbered according to the sequence of Feng et al., *Proc. Natl. Acad. Sci. USA*, 89:5447–5451 (1992).

TABLE 1

| REGIONS OF INTEREST FROM PUBLISHED SEQUENCES: | | | SEQ. ID NO: |
|---|---|---|---|
| EPEAKGRSKQEAR NAAAKLAVDIL | MURINE | PKR 51-74 | 30 |
| EPEGEGRSKKEAK NAAAKLAVEIL | HUMAN | PKR 52-75 | 27 |
| YGTGSGVTKQEAK QLAAKEAYQKL | MURINE | PKR 137-160 | 28 |
| YSIGTGSTKQEAK QLAAKLAYLQI | HUMAN | PKR 142-165 | 29 |
| GSGTSKKLAKRNAAAK | HUMAN | TAR RNA BINDING PROTEIN | 17 |

| PEPTIDES TESTED: | | | SEQ. ID NO: |
|---|---|---|---|
| AKGRSKQEARNAAAKLAVDIL | MURINE | PKR SITE 1(R1) | 13 |
| YGTGSGSTKQEAKQLAAKEAYQK | MURINE/HUMAN | PKR SITE 2 | 14 |
| GEGRSKKEAKNAAAKLAVEILNKEKK | HUMAN | PKR SITE 1 | 26 |
| KKEAKNAAAKLAVEILNKEKK | HUMAN | PKR SITE 1(hR1) | 15 |
| KQEAKQLAAKEAYQKLLK | MURINE | PKR SITE 2 | 16 |
| AKGRSKQEAR | MURINE | PKR SITE 1 | 1 |
| GRSKQEAR | | CONSENSUS | 8 | between PKR and TAR RNA because it was not observed in the absence of PKR and it was markedly prevented (60%) by excess levels of unlabeled poly(I)-poly(C) (80 μg/ml) used as a specific competitor to TAR RNA. The addition of either the hR1 (SEQ ID NO:15) or the R1 (400 μM)(SEQ ID NO:13) peptides greatly reduced TAR RNA-PKR complex formation.

EXAMPLE 4

Example 4 describes the specificity of PKR peptide antagonist interaction with dsRNA.

To examine more-closely the specificity of the R1-peptide (SEQ ID NO:13), several other synthetic peptides were utilized in protein kinase and RNA mobility-shift assays. Among these were peptides 271 (SEQ ID NO:22) and 273 (SEQ ID NO:23), each of which have similar composition and reverse-phase chromatographic properties to the R1-peptide (SEQ ID NO:13). Peptide 274 (SEQ ID NO:24) was an additional control, synthesized as a random R1 peptide (SEQ ID NO:13). Under conditions in which R1 (SEQ ID NO:13) or hR1 peptide (400 μM)(SEQ ID NO:15) markedly prevent the poly(I)-poly(C) dependent phosphorylation of PKR, peptides 271 (SEQ ID NO:22), 273 (SEQ ID NO:23), or 274 (SEQ ID NO:24) (600 μM) had no significant effect. None of the peptides 271 (SEQ ID NO:22), 273 (SEQ ID NO:23), or 274 (SEQ ID NO:24) formed a demonstrable complex with TAR RNA under conditions where a TAR RNA, R1 (SEQ ID NO:13), or hR1 (SEQ ID NO:15) peptide complex was clearly evident.

Regions of interest implicated in the antagonist study were aligned and compared to a region of the human TAR RNA binding protein. These were compared to peptides which demonstrated an ability to bind to poly(I)-poly(C) or TAR RNA and to antagonize activation of PKR. A peptide comprising the consensus sequence (SEQ ID NO:1) and consisting of murine PKR Site 1 sequences 54–63 was synthesized. Surprisingly, SEQ ID NO:1 both inhibited PKR activation and bound to TAR-RNA. Thus, SEQ ID NO:1 imitated the entire R1 peptide (SEQ ID NO:13).

Taken together, these findings suggest that R1-peptide specifically prevents the phosphorylation and activation of PKR. Moreover, this appears to be due to a direct interaction of the peptide with the site on dsRNA to which PKR normally binds.

EXAMPLE 5

Example 5 describes the stimulation of cell proliferation by a cell-permeable PKR peptide antagonist.

3T3F44A fibroblast cells were cultured in multiwell plates using medium containing 10% fetal bovine serum (FBS). Cell proliferation was measured in triplicate wells 1 day prior to confluence, at confluence, and 1 and 2 days after confluence, by removing the cells with 0.1% trypsin in phosphate-buffered saline and counting the suspended cells in Coulter Counter (Coulter Electronics, Inc.). Control cells remained in medium containing 10% FBS over the course of the experiment, while treated cells were grown in the same medium to which a PKR peptide antagonist (25 ug/ml final concentration) having the sequence AAVALLPAVLLAL- LAPKKEAKNAAAKLAVEILNKEKK (SEQ ID NO:24) had been added daily. The values cited here are the average of two identically performed experiments. One day prior to confluence, (Day −1), control cells numbered 1.3 million; at confluence (Day 0) control cells numbered 1.5 million; one day after confluence (Day 1) control cells numbered 1.6 million, and 2 days after confluence (Day 2) control cells numbered 1.7 million. In contrast, the PKR peptide antagonist-treated cells matched the control cell number on Day −1, but increased to 2 million at Day 0, and reached 2.2 million at Day 1 and Day 2. The 30% increase in cell number associated with PKR peptide antagonist treatment was statistically significant (p<0.05%) relative to untreated controls. Thus, the peptide antagonist of SEQ ID NO:24 which inhibits PKR activation also sustains the proliferation of 3T3F442A cells under conditions that normally result in cell cycle arrest.

EXAMPLE 6

Example 6 describes the uptake of a cell-permeable PKR peptide antagonist into 3T3F442A cells, the stability of the internalized peptide and its intracellular localization.

A PKR peptide antagonist (50 μg) having the sequence AAVALLPAVLLALLAPYPYDVPDY-AKKEAKNAAAKLAVEILNKEKK (SEQ ID NO: 25) comprising a cell permeability subsequence (residues 1–16 of SEQ ID NO:25), a heme agglutinin-epitope tag subsequence (residues 17–25 of SEQ ID NO:25), and a PKR peptide antagonist subsequence (residues 26–46 of SEQ ID NO:25) was radiolabeled with [$^{125}$I]-iodine by the chloramine-T method (Hunter, W. M. and Greenwood, F. C. Nature 194:495–496, 1962) and purified by size exclusion chromatography using BioGel P2 (BioRad, Inc.) 35 million CPM of radiolabeled PKR peptide was added to pre-confluent cultures of 3T3442A cells grown in medium containing 10% FBS. After 1 hour at 37° C., the media was aspirated and the cells were washed four times in phosphate buffered saline (PBS). Cells were removed from the culture dishes by scraping and collected by centrifugation (4EC, 750×g, 5 min). The wash buffer was removed and the cell pellet was dissolved in SDS-polyacrylamide gel buffer (Laemmli, Nature (London), 227:680–685, 1970). The sample was analyzed by SDS-tricine polyacrylamide gel electrophoresis using 4–20% gradient tricine-SDS gels and the radiolabeled peptide antagonist was visualized by autoradiography of dried gels. The size of the internalized radiolabeled peptide was compared with the radiolabeled starting material and a sample of the same peptide before radiolabeling, visualized in the same gels by Coomassie Blue staining. All three samples were identical in size, indicating that the radiolabeled PKR peptide antagonist remained intact after internalization by 3T3442A cells for at least one hour.

The subcellular localization of the PKR peptide antagonist (SEQ ID NO:25) that had been internalized by 3T3442A cells was determined by confocal microscopy. 3T3442A cells were cultured and treated with the PKR peptide antagonist (SEQ ID NO:25) for one hour at 37EC, while control cultures were left untreated and processed in parallel. Samples were fixed, permeabilized in methanol (Warrener and Petryshyn, *Biochem. Biophys. Res. Comm.*, 180:716–723 (1991)), and murine monoclonal antibodies to the HA sequence (Boehringer Mannheim) were used for immunofluorescent staining. Confocal microscopy revealed that the control cell samples showed little or no antibody staining, while PKR peptide antagonist-treated cell samples displayed obvious, intense localization of the epitope-tagged peptide to the cell cytoplasm. Taken together, the results in this example demonstrate that a cell-permeable PKR peptide antagonist is internalized by living cells, remains intact for at least one hour, and is localized to the specific region of the cell known to contain PKR and regulatory dsRNA.

EXAMPLE 7

Example 7 describes the anti-cytotoxic, cell-protective, growth promoting effect of PKR antagonists upon administration to HIV-1 infected cells.

The cell-permeable PKR peptide antagonist-comprising SEQ ID NO:31 was administered to the human lymphoblastoid cell line MT-4 which were infected with HIV-1 retrovirus. The cells were maintained in tissue culture conditions which promoted the productive growth of the virus, thus promoting the lysis of cells and release of infective virus. The cells were infected with high doses of HIV-1 virus: 100 and 1000 "TCPD$_{50}$" units of virus (one "TCPD$_{50}$" unit is the tissue culture pathogenic dose of virus capable of causing 50% lysis (death) of cells). The PKR peptide agonist comprising SEQ ID NO:24 was tested over a wide range of concentrations: 4, 20 and 100 micrograms per ml. Results of this experiment are presented in Table 2.

TABLE 2

% of Cell Death by HIV-1 Infection

| Peptide Concentration (ugm/ml) | 1000 TCPD$_{50}$ units | 100 TCPD$_{50}$ units |
|---|---|---|
| 0 | 100% | 80% |
| 4 | 25% | 10% |
| 20 | 30% | 16% |
| 100 | 40% | 25% |

The data (Table 2) demonstrates that the cell-permeable PKR peptide antagonist SEQ ID NO:31 significantly reduced cell lysis (and thus, cell death) resulting from HIV-1 pathogenesis. Survival of MT-4 cells after infection with the 100 TCPD$_{50}$ units dose of HIV-1 was: 0% (control), 75%, 70% and 60% at 0, 4, 20 and 100 microgram per ml of PKR peptide antagonist SEQ ID NO:31. Survival of MT-4 cells after infection with the 1000 TCPD$_{50}$ units dose of HIV-1 was: 20% (control), 90%, 84% and 75% at 0, 4, 20 and 100 microgram per ml of PKR peptide antagonist SEQ ID NO:31.

Thus, the PKR antagonists of the invention can promote HIV-1-infected cell proliferation and reduce HIV-1-infected cell lysis. The therapeutic benefit of such an administration is beneficial in maintaining the immune system of patients suffering from HIV-1 infection, as HIV-1 pathogenesis is characterized by decreased cell proliferation and loss of (lysis of) HIV-1 infected lymphocytes and other HIV-1 cells. The therapeutic benefit of such an administration is beneficial in preventing the lysis of virus-infected cells in general. The therapeutic benefit of such an administration can also be beneficial by promoting cell proliferation in diseases or syndromes whose pathogenesis includes cell cycle arrest, quiescence, reduced growth or cell death.

EXAMPLE 8

Example 8 describes another aspect of the anti-cytotoxic, cell-protective effect of PKR antagonists upon administration to HIV-1 infected cells: exposure of HIV-1 infected cells to the PKR peptide antagonist SEQ ID NO:31 results in an increase in number of cells expressing the CD4 receptor compared to untreated cells.

Another aspect of the cell-protective, anti-cytolytic effect of PKR peptide antagonist SEQ ID NO:31 on HIV-1-infected MT-4 cells can be seen by analyzing the phenotype of the surviving cells. Surviving cells were analyzed for CD4+ expression by conventional immunodetection techniques. The data is summarized in Table 3.

TABLE 3

Expression of CD4 in HIV-1 Infected MT-4 Cells after Agonist Administration

| Peptide Concentration (ugm/ml) | % CD4+ Positive Cells |
|---|---|
| 0 | 85% |
| 4 | 100% |
| 20 | 100% |
| 100 | 100% |

The data (Table 3) indicates that exposure of MT-4 cells to the PKR peptide antagonist SEQ ID NO:31 results in an increase in number of cells expressing the CD4 receptor compared to untreated cells. The PKR antagonist can be increasing expression of CD4 or it can be maintaining the expression of CD4 on the cell surface of the lymphoblastoid cells. The therapeutic benefit of such an administration is beneficial in maintaining the immune system of patients suffering from HIV-1 infection, as HIV-1 pathogenesis is characterized by loss of CD4 positive cells. The therapeutic benefit of such an administration can also be beneficial by maintaining the expression of or increasing the expression of CD4+ on cells in diseases or syndromes whose pathogenesis includes loss of CD4+-expressing cells.

All publications and patents mentioned in this specification are herein incorporated by reference into the specification to the same extent as if each individual publication or patent was specifically and individually indicated to be incorporated herein by reference.

What is claimed is:

1. An isolated double-stranded RNA dependent protein kinase (PKR) peptide antagonist of less than 50 amino acid residues in length and comprising at least 8 contiguous amino acid residues from a sequence selected from the group consisting of: SEQ ID NO:1, SEQ ID NO:2, SEQ ID NO:3, SEQ ID NO:4, SEQ ID NO:5 and SEQ ID NO:6, wherein PKR peptide antagonist activity is demonstrated by the formation of a complex between the peptide antagonist and double-stranded RNA.

2. The PKR peptide antagonist of claim 1, wherein said PKR peptide antagonist comprises at least 9 continuous residues from a sequence selected from the group consisting of SEQ ID NO:1, SEQ ID NO:2, SEQ ID NO:3, SEQ ID NO:4, SEQ ID NO:5 and SEQ ID NO:6.

3. The PKR peptide antagonist of claim 1, wherein said antagonist comprises a sequence selected from the group consisting of SEQ ID NO:1, SEQ ID NO:2, SEQ ID NO:3, SEQ ID NO:4, SEQ ID NO:5 and SEQ ID NO:6.

4. The PKR peptide antagonist of claim 1, comprising no more than 25 amino acids.

5. The PKR peptide antagonist of claim 1, wherein said PKR peptide antagonist comprises SEQ ID NO:1.

6. The PKR peptide antagonist of claim 1, wherein said PKR peptide antagonist comprises SEQ ID NO:2.

7. The PKR peptide antagonist of claim 1, wherein said PKR peptide antagonist comprises SEQ ID NO:3.

8. The PKR peptide antagonist of claim 1, wherein said PKR peptide antagonist comprises SEQ ID NO:4.

9. The PKR peptide antagonist of claim 1, wherein said PKR peptide antagonist comprises SEQ ID NO:5.

10. The PKR peptide antagonist of claim 1, wherein said PKR peptide antagonist comprises SEQ ID NO:6.

11. The PKR peptide antagonist of claim 1, wherein said PKR peptide antagonist comprises SEQ ID NO:7.

12. The PKR peptide antagonist of claim 1, wherein said PKR peptide antagonist comprises SEQ ID NO:8.

13. The PKR peptide antagonist of claim 1, wherein said PKR peptide antagonist comprises SEQ ID NO:9.

14. The PKR peptide antagonist of claim 1, wherein said PKR peptide antagonist comprises SEQ ID NO:10.

15. The PKR peptide antagonist of claim 1, wherein said PKR peptide antagonist comprises SEQ ID NO:11.

16. The PKR peptide antagonist of claim 1, wherein said PKR peptide antagonist comprises SEQ ID NO:12.

17. The PKR peptide antagonist of claim 1, wherein said PKR peptide antagonist comprises SEQ ID NO:13.

18. The PKR peptide antagonist of claim 1, wherein said PKR peptide antagonist comprises SEQ ID NO:14.

19. The PKR peptide antagonist of claim 1, wherein said PKR peptide antagonist comprises SEQ ID NO:15.

20. The PKR peptide antagonist of claim 1, wherein said PKR peptide antagonist comprises SEQ ID NO:16.

21. The PKR peptide antagonist of claim 1, wherein said PKR peptide antagonist comprises SEQ ID NO:17.

22. The PKR peptide antagonist of claim 1, wherein said PKR peptide antagonist comprises SEQ ID NO:18.

23. The PKR peptide antagonist of claim 1, wherein said PKR peptide antagonist comprises SEQ ID NO:26.

24. The PKR peptide antagonist of claim 1, wherein said PKR peptide antagonist comprises the cell permeability subsequence shown in SEQ ID NO:19.

25. The PKR peptide antagonist of claim 24, wherein said PKR peptide antagonist comprises SEQ ID NO:20.

26. The PKR peptide antagonist of claim 24, wherein said PKR peptide antagonist comprises SEQ ID NO:21.

27. The PKR peptide antagonist of claim 24, wherein said PKR peptide antagonist comprises SEQ ID NO:25.

28. The PKR peptide antagonist of claim 24, wherein said PKR peptide antagonist comprises SEQ ID NO:31.

29. A method of antagonizing regulatory RNA binding to double-stranded RNA dependent protein kinase (PKR), said method comprising contacting a PKR peptide antagonist of less than 50 amino acids in length with a double-stranded RNA to form a double-stranded RNA-antagonist complex, wherein said PKR peptide antagonist is inclusive of at least 8 contiguous amino acid residues from a sequence selected from the group consisting of: SEQ ID NO:1, SEQ ID NO:2, SEQ ID NO:3, SEQ ID NO:4, SEQ ID NO:5, and SEQ ID NO:6, wherein said method is performed ex vivo.

30. The method of claim 29, wherein said PKR peptide antagonist comprises at least 9 contiguous residues from a sequence selected from the group consisting of SEQ ID NO:1, SEQ ID NO:2, SEQ ID NO:3, SEQ ID NO:4, SEQ ID NO:5, and SEQ ID NO:6.

31. The method of claim 29, wherein said PKR peptide antagonist comprises a sequence selected from the group consisting of SEQ ID NO:1, SEQ ID NO:2, SEQ ID NO:3, SEQ ID NO:4, SEQ ID NO:5, and SEQ ID NO:6.

32. The method of claim 29, wherein said PKR peptide antagonist consists essentially of a sequence selected from the group consisting of SEQ ID NO:1, SEQ ID NO:2, SEQ ID NO:3, SEQ ID NO:4, SEQ ID NO:5, and SEQ ID NO:6.

33. The method of claim 29, wherein said PKR peptide antagonist comprises the cell permeability subsequence shown in SEQ ID NO:19.

34. The method of claim 29, wherein said method comprises contacting said PKR peptide antagonist with a double-stranded RNA within a eukaryotic cell.

35. The method of claim 34, wherein said PKR peptide antagonist is expressed by an expression vector encoding said PKR peptide antagonist.

36. The method of claim 34, wherein said method stimulates cell proliferation under conditions of cell cycle arrest, quiescence, reduced growth or cell death.

37. The method of claim 34, wherein the cell is a human cell.

38. The method of claim 34, wherein said method reduces cell death.

39. The method of claim 38, wherein said method reduces cell death by reducing cell lysis caused by a viral infection.

40. The method of claim 39, wherein said viral infection is an HIV-1 infection.

41. The method of claim 38, wherein cell death is reduced by inhibiting apoptosis.

42. The method of claim 29, wherein said PKR peptide antagonist comprises no more than 25 amino acids.

43. A method of reducing cell lysis caused by a viral infection, said method comprising contacting a PKR peptide antagonist of less than 50 amino acids in length with a double-stranded RNA to form a double-stranded RNA-antagonist complex, wherein said PKR peptide antagonist is inclusive of at least 8 contiguous amino acid residues from a sequence selected from the group consisting of: SEQ ID NO:1, SEQ ID NO:2, SEQ ID NO:3, SEQ ID NO:4, SEQ ID NO:5, and SEQ ID NO:6, wherein the method is performed ex vivo.

44. The method of claim 43, wherein said viral infection is an HIV-1 infection.

45. A method of inhibiting apoptosis, said method comprising contacting a PKR peptide antagonist of less than 50 amino acids in length with a double-stranded RNA to form a double-stranded RNA-antagonist complex, wherein said PKR peptide antagonist is inclusive of at least 8 contiguous amino acid residues from a sequence selected from the group consisting of: SEQ ID NO:1, SEQ ID NO:2, SEQ ID NO:3, SEQ ID NO:4, SEQ ID NO:5, and SEQ ID NO:6, wherein the method is performed ex vivo.

46. The method of claim 43 or 45, wherein the PKR peptide antagonist comprises SEQ ID NO:31.

47. An isolated double-stranded RNA dependent protein kinase (PKR) peptide antagonist of less than 50 amino acid residues in length and comprising at least 5 contiguous amino acid residues from a sequence selected from the group consisting of: SEQ ID NO:1, SEQ ID NO:2, SEQ ID NO:3, SEQ ID NO:4, SEQ ID NO:5 and SEQ ID NO:6, wherein double-stranded RNA dependent protein kinase (PKR) peptide antagonist activity is demonstrated by the formation of a complex between the peptide antagonist and double-stranded RNA.

* * * * *